(12) United States Patent
Ochiai et al.

(10) Patent No.: US 10,034,880 B2
(45) Date of Patent: Jul. 31, 2018

(54) OPHTHALMIC SUSPENSION FORMULATION

(71) Applicant: Sumitomo Dainippon Pharma Co., Ltd., Osaka-shi (JP)

(72) Inventors: Yasushi Ochiai, Osaka (JP); Yuka Kato, Osaka (JP); Maki Sasaki, Tokyo (JP); Takafumi Matsumoto, Osaka (JP)

(73) Assignee: Sumitomo Dainippon Pharma Co., Ltd., Osaka-shi (JP)

( * ) Notice: Subject to any disclaimer, the term of this patent is extended or adjusted under 35 U.S.C. 154(b) by 0 days.

(21) Appl. No.: 15/509,715

(22) PCT Filed: Sep. 10, 2015

(86) PCT No.: PCT/JP2015/075745
§ 371 (c)(1),
(2) Date: Mar. 8, 2017

(87) PCT Pub. No.: WO2016/039422
PCT Pub. Date: Mar. 17, 2016

(65) Prior Publication Data
US 2017/0296536 A1      Oct. 19, 2017

(30) Foreign Application Priority Data

Sep. 11, 2014    (JP) .................. 2014-185731

(51) Int. Cl.
| | | |
|---|---|---|
| *A61K 31/49* | (2006.01) |
| *A61K 31/499* | (2006.01) |
| *A61K 9/00* | (2006.01) |
| *A61K 9/10* | (2006.01) |

(52) U.S. Cl.
CPC .......... *A61K 31/499* (2013.01); *A61K 9/0048* (2013.01); *A61K 9/10* (2013.01)

(58) Field of Classification Search
None
See application file for complete search history.

(56) References Cited

U.S. PATENT DOCUMENTS 5,258,382 A  *  11/1993  Negoro ............... C07D 487/20
                                                            514/249
6,297,244 B1    10/2001  Ohashi et al.
2010/0216856 A1  8/2010  Chung et al.

FOREIGN PATENT DOCUMENTS

| JP | 2516147 B2 | 7/1996 |
| JP | 2005-97275 | 4/2005 |
| JP | 2009-196973 | 9/2009 |
| WO | WO 99/20276 A1 | 4/1999 |

(Continued)

OTHER PUBLICATIONS

Aldrich et al. (Ophthalmic Preparations, Aug. 28, 2013).*

(Continued)

*Primary Examiner* — Robert A Wax
*Assistant Examiner* — Melissa S Mercier
(74) *Attorney, Agent, or Firm* — Oblon, McClelland, Maier & Neustadt, L.L.P.

(57) ABSTRACT

The present invention relates to a stable ophthalmic suspension formulation comprising (R)-(−)-2-(4-bromo-2-fluorobenzyl)-1,2,3,4-tetrahydropyrrolo[1,2-a]pyrazine-4-spiro-3'-pyrrolidine-1,2',3,5'-tetrone, which is useful for treating a disease in posterior eye segment and the like, avoiding side-effects due to systemic exposure.

24 Claims, 8 Drawing Sheets

(56) References Cited

FOREIGN PATENT DOCUMENTS

WO    WO 2008/093691 A1    8/2008
WO    WO 2009/041566 A1    4/2009

OTHER PUBLICATIONS

International Search Report dated Nov. 17, 2015 in PCT/JP2015/075745 (English translation only).
International Preliminary Report on Patentability and Written Opinion dated Mar. 23, 2017 in PCT/JP2015/075745 filed Sep. 10, 2015 (English translation only ).
Yuuki Takashima, Drug Delivery to the Posterior Eye Segment The Archives of Practical Pharmacy (Journal of Pharmaceutical Science and Technology, Japan), 72(2), 2012, pages 117-121.
Standard Yakugaku Series 7 "Seizaikano Science", edited by The Pharmaceutical Society of Japan, issued by Tokyo Kagaku Doujin, Forth Chapter "Representative formulation" 22-2 Ophthalmic formulation, Feb. 10, 2006, pp. 103-105.
"*Tenganzai-no tekiseishiyou handbook Q & A*" prepared by The Pharmaceutical Manufacturers' Association of Tokyo, Tenganzai kenkyukai, and others, supervised by Japan Ophthalmologists Association, Sep. 2011 first edition, 24 page.
Yoshihisa Shirasaki, Study to identify orally bioavailable calpain inhibitors to develop an agent for treating a retinal disease Doctoral thesis abstracts, Abstract of Dissertation and Abstract of Examination outcome, pp. 605-610, Sep. 2007, (with English abstract).
Akihiro Kakehashi, et al., "Prophylactic Medical Treatment of Diabetic Retinopathy", Diabetic Retinopathy, InTech, 2012, pp. 291-304 and cover page.
Fumihiko Toyoda, "Effect of Ranirestat, a New Aldose Reductase Inhibitor, on Diabetic Retinopathy in SDT Rats", Journal of Diabetes Research, vol. 2014, Article Id 672590, 2014, 8 pages.
Toshiyuki Negoro, et al., "Novel, Highly Potent Aldose Reductase Inhibitors. (R)—(−)-2-(4-Bromo-2-fluorobenzyl)-1,2,3,4-tetrahydropyrrolo[1,2-a] pyrazine-4-spiro-3'-pyrrolidine-1,2',3,5'-tetrone (AS-3201) and Its Congeners", J. Mod. Chem. 1998, vol. 41, pp. 4118-4129.
Otto Hockwin, et al., "Determination of AL01576 Concentration in Rat Lenses and Plasma by Bioassay for Aldose Reductase Activity Measurements", Ophthalmic Res., 1989, vol. 21, pp. 285-291.
Peter F. Kador, et al., "Topical Aldose Reductase Inhibitor Formulations for Effective Lens Drug Delivery in a Rat model for Sugar Cataracts", Journal of Ocular Pharmacology and Therapeutics, vol. 23, No. 2, 2007, pp. 116-123.
Hideo Terayama, et al., "Preparation of Stable Aqueous Suspension of a Hydrophobic drug with Polymers", Colloids and Surfaces B.: Biointerfaces, 39, 2004, pp. 159-164.
Extended European Search Report dated Mar. 21, 2018 in Patent Application No. 15840591.0, 7 pages.

\* cited by examiner

OPHTHALMIC SUSPENSION FORMULATION

TECHNICAL FIELD

The present invention mainly relates to an ophthalmic suspension formulation comprising (R)-(−)-2-(4-bromo-2-fluorobenzyl)-1,2,3,4-tetrahydropyrrolo[1,2-a]pyrazine-4-spiro-3′-pyrrolidine-1,2′,3,5′-tetrone, particularly which is useful for a disease in posterior eye segment.

BACKGROUND ART

The posterior eye segment tissue such as vitreous body, retina, choroid, and sclera is an important domain for visual performance. If the domain is damaged, it may often cause severely-reduced visual acuity or visual loss. Typical diseases in posterior eye segment include age-related macular degeneration, diabetic retinopathy, diabetic macular edema, macular edema, myopic choroidal neovascularization, retinal vein occlusion, choroidal neovascularization, uveitis, retinitis pigmentosa, proliferative vitreoretinopathy, and central serous chorioretinopathy. In particular, age-related macular degeneration or diabetic retinopathy is main diseases causing visual loss in late-middle-aged to senile people in developed countries such as Europe, America, and Japan, which is a very problematic disease in ophthalimic clinic and also in whole society (Patent Literature 1).

In general, the drug delivery to the posterior eye segment such as retina via blood is severely limited with blood-retinal barrier (BRB) in the posterior eye segment. When a drug is administered in eyedrops, most of the drug can be quickly discharged from the eye surface by tear-turnover and then transferred to blood in general-circulation via nasolacrimal canal (Non-Patent Literature 1). Thus, if the amount of a drug in an ophthalmic formulation is 100, the amount of the delivered drug administered in eyedrops is 0.1-0.5 in cornea to which the drug is most transferred; 0.01-0.1 in anterior aqueous humor/iris and ciliary; and about 0.0001 in lens and vitreous body, i.e., it has been known that the delivered amount is too low (Non-Patent Literature 2). In addition, it is generally thought that a drug can be hardly delivered to the posterior eye segment by the administration in eyedrops because the posterior eye segment locates in further back of lens or vitreous body. And, it is generally thought that an ophthalmic suspension which is used in case of a low-water-soluble drug is more difficult to be delivered to the posterior eye segment by the administration in eyedrops than a normal ophthalmic solution, because such drug is not dissolved in water and thus it is generally hardly absorbed into intraocular site (Non-Patent Literature 3). There are some ophthalmic suspensions in clinical practice, but the use is limited in a disease in anterior eye segment such as conjunctivitis. It is thought that the means to make a drug delivered to the posterior eye segment are only an injection into vitreous body or a surgery, or a systemic administration via general circulation blood, i.e., the other means are very difficult (Patent Literature 4, Non-Patent Literature 4).

A disease in posterior eye segment is an eye disease causing a severe symptom, but there are few useful drugs for it, and furthermore the administration is limited because the targeting site is the posterior eye segment where a drug is hard to be delivered. Thus, the treatment for the disease is now done by the injection of an anti-vascular endothelial growth factor (anti-VEGF) into vitreous body, the injection of a steroid into vitreous body or Tenon capsule, the photodynamic therapy (PDT), the surgery of vitreous body, etc. However, all of these current treatments, i.e., injection into eyes, etc., are very invasive for patients, and inflict pain to patients, thus it has been desired to develop a new administration such as eyedrops.

(R)-(−)-2-(4-bromo-2-fluorobenzyl)-1,2,3,4-tetrahydropyrrolo[1,2-a]pyrazine-4-spiro-3′-pyrrolidine-1,2′,3,5′-tetrone (ranirestat) (hereinafter, defined as "Compound A") has a potent action inhibiting aldose reductase, and the compound is also a low-toxic compound, thus the compound are useful as a drug for treating diabetic complication (Patent Literature 2, Patent Literature 3).

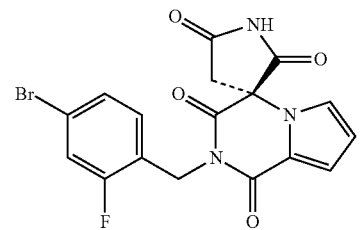

PRIOR ART

Patent Reference

[Patent Literature 1] JP 2009-196973 A
[Patent Literature 2] JP 2516147 B
[Patent Literature 3] WO 1999/020276
[Patent Literature 4] JP 2005-097275 A Non-Patent Reference

[Non-Patent Literature 1] "Drug Delivery to the Posterior Eye Segment" Yuuki TAKASHIMA, The archives of practical pharmacy, 72(2), 117-121 (2012)

[Non-Patent Literature 2] Standard Yakugaku Series 7 "Seizaikano Science", edited by The Pharmaceutical Society of Japan, issued by Tokyo Kagaku Doujin, Forth Chapter "Representative formulation" 22-2 Ophthalmic formulation, p 103-p 105

[Non-Patent Literature 3] "Tenganzai-no tekiseishiyou handbook Q & A" prepared by The Pharmaceutical Manufacturers' Association of Tokyo, Tenganzai kenkyukai, and others, supervised by JAPAN OPHTHALMOLOGISTS ASSOCIATION, September in 2011 first edition, page 5

[Non-Patent Literature 4] "Study to identify orally bioavailable calpain inhibitors to develop an agent for treating a retinal disease" Yoshihisa SHIRASAKI, Graduate School of Natural Science & Technology, Doctoral thesis abstracts, Abstract of Dissertation and Abstract of Examination outcome, P 605-p 610, issued in September, 2007.

SUMMARY OF INVENTION

Technical Problem

In order to deliver an effective concentration of a drug to the posterior eye segment via general circulation blood, it is thought be necessary to enhance the drug concentration in general circulation blood by administering a very high dose thereof because of the blood-retinal barrier (BRB). In order to avoid the risk of such high dose, the object of the present invention is to provide an ophthalmic formulation useful for the disease in posterior eye segment and avoiding side-effects due to high-dose systemic exposure, and additionally a stable ophthalmic formulation comprising Compound A or a physiologically-acceptable salt thereof.

Solution to Problem

The present inventors have extensively studied to reach the above object, and then have found that the eyedrop-administration of a suspension of Compound A or a physiologically-acceptable salt thereof in a dispersion medium can make the drug delivered to the posterior eye segment in a high transferability needed for the treatment while keeping the stability of the drug and supressing the amount of systemic exposure, and additionally has found that Compound A or a physiologically-acceptable salt thereof has a useful pharmacological action for an eye disease such as age-related macular degeneration. Namely, the present invention has been completed by suspending Compound A or a physiologically-acceptable salt thereof as an ophthalmic formulation.

The summary of the present invention is described as follows.

(Term 1)
An ophthalmic suspension formulation comprising (R)-(–)-2-(4-bromo-2-fluorobenzyl)-1,2,3,4-tetrahydropyrrolo[1,2-a]pyrazine-4-spiro-3'-pyrrolidine-1,2',3,5'-tetrone (hereinafter, referred to as "Compound A") or a physiologically-acceptable salt thereof.

(Term 2)
The formulation of Term 1, wherein Compound A or a physiologically-acceptable salt thereof is dispersed in a dispersion medium.

(Term 3)
The formulation of Term 2, wherein the mean particle size of Compound A or a physiologically-acceptable salt thereof in the suspension is from 1 nm to 20 μm.

(Term 4)
The formulation of Term 3, wherein the mean particle size of Compound A or a physiologically-acceptable salt thereof in the suspension is from 10 nm to 20 μm.

(Term 5)
The formulation of any one of Terms 2 to 4, wherein the dispersion medium is an aqueous dispersion medium.

(Term 6)
The formulation of any one of Terms 2 to 5, wherein the dispersion medium comprises a dispersant and/or a surfactant.

(Term 7)
The formulation of Term 6, wherein the dispersion medium comprises a dispersant and a surfactant.

(Term 8)
The formulation of any one of Terms 2 to 7, wherein the pH of the suspension is 3 to 9.

(Term 9)
The formulation of any one of Terms 2 to 8, wherein the osmotic pressure of the suspension is 20 mOsm to 1000 mOsm.

(Term 10)
The formulation of any one of Terms 2 to 9, which comprises 1 mg to 500 mg of Compound A or a physiologically-acceptable salt thereof per 1 mL of the suspension.

(Term 11)
The formulation of any one of Terms 2 to 10, wherein the ratio of Compound A or a physiologically-acceptable salt thereof dissolved in the suspension to all of Compound A or a physiologically-acceptable salt thereof in the formulation is 0.001% to 10%.

(Term 12)
The formulation of any one of Terms 2 to 11, wherein the ratio of Compound A or a physiologically-acceptable salt thereof dissolved in the suspension to all of Compound A or a physiologically-acceptable salt thereof in the formulation is 0.001% to 1%.

(Term 13)
The formulation of any one of Terms 1 to 12, which is used for treating a disease in anterior eye segment and/or a disease in posterior eye segment.

(Term 14)
The formulation of Term 13, wherein the disease is a disease related to VEGF.

(Term 15)
The formulation of Term 13 or 14, wherein the disease is age-related macular degeneration, diabetic retinopathy, diabetic macular edema, myopic choroidal neovascularization, retinal vein occlusion and/or cataract.

(Term 16)
A kit comprising a combination of (1) a formulation comprising Compound A or a physiologically-acceptable salt thereof, and (2) a formulation comprising a dispersion medium.

(Term 17)
The kit of Term 16, wherein the mean particle size of Compound A or a physiologically-acceptable salt thereof in formulation (1) is from 1 nm to 20 μm.

(Term 18)
The kit of Term 17, wherein the mean particle size of Compound A or a physiologically-acceptable salt thereof in formulation (1) is from 10 nm to 20 μm.

(Term 19)
The kit of any one of Terms 16 to 18, wherein formulation (1) or formulation (2) may comprise a dispersant and/or a surfactant.

(Term 20)
The kit of any one of Terms 16 to 19, which is used for treating a disease in anterior eye segment and/or a disease in posterior eye segment.

(Term 21)
A medicament for treating a disease related to VEGF, comprising Compound A or a physiologically-acceptable salt thereof.

(Term 22)
The medicament of Term 21, wherein the disease is age-related macular degeneration and/or diabetic retinopathy.

(Term 23)
The formulation of any one of Terms 2 to 4, wherein the suspension comprises a dispersant and/or a surfactant.

(Term 24)
The formulation of Term 23, wherein the suspension comprises a dispersant and a surfactant.

Effect of the Invention

The present invention can provide a stable ophthalmic formulation comprising Compound A or a physiologically-acceptable salt thereof, which has a therapeutic action for not only a disease in anterior eye segment, but also a disease in posterior eye segment, and can avoid side-effects due to high-dose systemic exposure. The solubility of Compound A in water is low, thus if preparing a water-solution formulation comprising Compound A, the concentration thereof should be low. By preparing a formulation comprising Compound A as a suspension, however, the formulation will become a highly-concentrated one, which is expected to deliver a sufficient amount of the drug to a diseased site with a realistic frequency of administration, for example, once to 6 times a day. In addition, Compound A has another problem that the stability in solution state is very bad and the compound in a solution can decompose in hours, but a suspension formulation comprising Compound A can provide an ophthalmic formulation thereof that has an ability to endure the decomposition and also has a good stability for actual storage. The present ophthalmic formulation can provide a breakthrough treatment for a disease in posterior eye segment that has been treated mainly by an invasive method, in less burden for patients.

Figure 1:
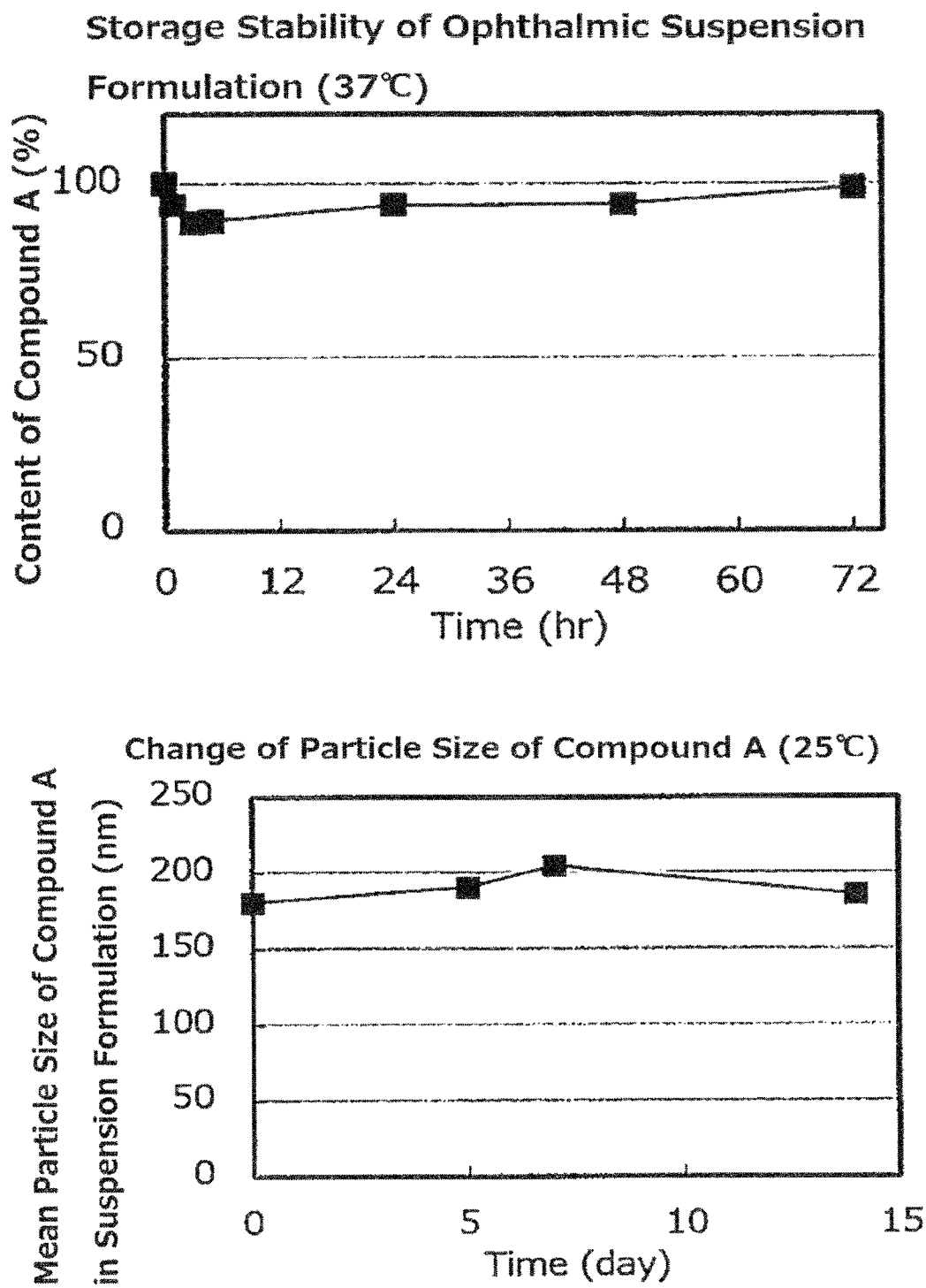
FIG. 1 shows results of the storage stability about the content and particle size of Compound A in the ophthalmic suspension formulation. The vertical axis of the upper graph denotes the content (%) of Compound A in the suspension formulation, and the abscissa axis thereof denotes time (hr). The vertical axis of the lower graph denotes the mean particle size (nm) of Compound A in the suspension formulation, and the abscissa axis thereof denotes time (day).

The "mean±se" at upper right in FIG. 2, FIG. 3, FIG. 4-FIG. 9 means that each indicated value denotes mean value in each group and each error range denotes se (standard error). The "n" means the number of specimen per group.

DESCRIPTION OF EMBODIMENTS

The present formulation is an ophthalmic formulation, which is characterized in that Compound A or a physiologically-acceptable salt thereof (hereinafter, it may be referred to as "the present drug" as a whole) is suspended in a dispersion medium. The present formulation includes an ophthalmic suspension comprising Compound A or a physiologically-acceptable salt thereof and a dispersion medium, and a kit to prepare a suspension in use by dispersing Compound A or a physiologically-acceptable salt thereof in a dispersion medium.

The active ingredient in the present formulation, Compound A may be in a free form or in a salt form with a physiologically-acceptable, i.e., pharmaceutically-acceptable inorganic or organic base. The inorganic and organic bases include, for example, an alkali metal such as sodium and potassium, ammonium hydroxide, isopropylamine, diethylamine, ethanolamine, piperidine, and lysine. And, Compound A or a physiologically-acceptable salt thereof of the present invention may also be in a form of hydrate or solvate, thus Compound A or a physiologically-acceptable salt thereof in the present invention encompasses such hydrate and solvate. The details thereof are described in Patent Literature 2. Compound A or a physiologically-acceptable salt thereof can be prepared, for example, according to Patent Literature 2.

The term "suspension" used herein means a state where Compound A or a physiologically-acceptable salt thereof is dispersed as a solid in a dispersion medium, which also includes a suspension wherein the present drug is partially dissolved in a dispersion medium. If the present drug is precipitated or aggregated in a suspension due to a storage, the suspension can be loosely shaken before the use to recover to the regular suspension state, which is also encompassed in the present suspension. However, the present invention does not encompass a formulation wherein the drug is dispersed, emulsified or encapsulated in an oil and fat liquid drop, such as liposome and emulsion formulations. Specifically, the drug particle in the present formulation does not need to be coated with fat or oil ingredient, and the present invention does not encompass, for example, a suspension formulation wherein the present drug is encapsulated in liposome, or an oil-in-water emulsion formulation wherein an oil and fat liquid drop comprising the present drug is dispersed in water.

The ratio of Compound A or a physiologically-acceptable salt thereof dissolved in the suspension to all of Compound A or a physiologically-acceptable salt thereof in the formulation is generally 0.001% to 10%, preferably 0.001% to 5% from the viewpoint of the transferability to the retina in posterior eye segment, the chemical stability, and the physical stability of particle size, etc., further preferably 0.001% to 2%, more preferably 0.001% to 1%, even more preferably 0.001% to 0.5%, and especially preferably 0.001% to 0.1%. Preferably, the present formulation does not include an ingredient having a solubilizing action to enhance the solubility of the present drug as an additive, but may include such ingredient having a solubilizing action unless the amount of the ingredient can affect the solubility of the present drug. Such ingredient having a solubilizing action includes, for example, cyclodextrin.

The "dispersion" herein means a state where Compound A or a physiologically-acceptable salt thereof is uniformly suspended in a dispersion medium, which also includes a temporary suspension and a partially-aggregated suspension unless they pose a problem for use as ophthalmic formulation.

The mean particle size of solid Compound A or a physiologically-acceptable salt thereof suspended in a suspension formulation should not be limited, but, from the viewpoint of manufacturing treatability and transferability to posterior eye segment, it is preferably 20 μm or less, more preferably 2 μm or less, even more preferably 700 nm or less, even more preferably 650 nm or less, even more preferably 460 nm or less, even more preferably 300 nm or less, even more preferably 230 m or less, and especially preferably 200 nm or less.

And, the mean particle size of solid Compound A or a physiologically-acceptable salt thereof suspended in the present suspension formulation is preferably 1 nm or more, more preferably 5 nm or more, and even more preferably 10 nm or more. The range of the mean particle size is preferably 10 nm to 20 μm or 1 nm to 20 μm, more preferably 10 nm to 2 μm or 1 nm to 2 μm, more preferably 10 nm to 700 nm or 1 nm to 700 nm, even more preferably 1 nm to 650 nm, further preferably 1 nm to 460 nm, even more preferably 1 nm to 300 nm, even more preferably 10 nm to 300 nm or 5 nm to 300 nm, even more preferably 1 nm to 230 nm, even more preferably 5 nm to 230 nm, even more preferably 5 nm to 200 nm, and especially preferably 10 nm to 200 nm or 10 nm to 230 nm.

The mean particle size used herein means a mean particle size of Compound A or a physiologically-acceptable salt thereof, a micronized Compound A or a physiologically-acceptable salt thereof, or a solid Compound A or a physiologically-acceptable salt thereof suspended in a suspension formulation. The mean particle size used herein means a mean particle size obtained with the devices and methods mentioned below. When the mean particle size is measured in a suspension formulation, the concentration of the suspension may be diluted to a measurable concentration thereof.

The above-mentioned Compound A or a physiologically-acceptable salt thereof having an acceptable particle size can be prepared by wet milling or dry milling.

The preparation by wet milling can be done by stirring or dispersing the compound in a suitable solvent (for milling) with a stirrer, a homogenizer, etc. Or, the milled compound can be prepared by milling the compound in a suitable solvent (for milling) with a wet jet mill such as Star Burst, as well as a ball mill, a beads mill, a homomixer, a homogenizer, and the like. For example, Compound A or a physiologically-acceptable salt thereof in a solvent for milling can be milled with a planetary ball mill (LP-4/2, ITO MANUFACTURING CO., LTD.) wherein the content of the compound is 1-500 mg/mL, and the speed is 30-370 rpm.

The preparation by dry milling can be done with an airflow-type pulverizer such as spiral jet mill, Jet-O-Mill, counter jet mill, and jet mill; a shear-type pulverizer such as hammer mill, screen mill, and sample mill; a rolling ball mill such as ball mill and beads mill; etc.

In addition, the milled Compound A or a physiologically-acceptable salt thereof used herein can be also prepared by a build-up method using spray-dry, crystallization, or lyophilization, besides a break-down method which makes the particle smaller by dispersing, milling, etc.

The ophthalmic formulation can be categorized in the present invention if the formulation is/becomes a suspension state for eyedrops in the latest step. For example, in case of preparing the present formulation by dry milling, Compound A or a physiologically-acceptable salt thereof can be milled with the above-mentioned milling device to make the particle size a desired one, specifically, each above-defined mean particle size, and then suspended in a dispersion medium to obtain the formulation. The formulation of the present invention also includes an embodiment of preparing a suspension in use (i.e., a kit), that is, separately preparing Compound A or a physiologically-acceptable salt thereof and a dispersion medium, and suspending the Compound A or a physiologically-acceptable salt thereof in the dispersion medium in use.

In case of preparing the present formulation by wet milling, a mixture of Compound A or a physiologically-acceptable salt thereof and a solvent for milling can be milled with the above-mentioned milling device, the solvent for milling can be removed by lyophilization or other means, and then the lyophilized product can be suspended in a dispersion medium to obtain the formulation. The formulation of the present invention also includes an embodiment of separately preparing the lyophilized product and a dispersion medium, and suspending the lyophilized product in the dispersion medium in use (i.e., a kit). Namely, a kit comprising a combination of (1) a lyophilized composition comprising the present drug, and (2) a dispersion medium is also in the present embodiment. As shown below, when Compound A or a physiologically-acceptable salt thereof is milled with a solvent for milling comprising a surfactant, a dispersant and the like and the solvent for milling is removed by lyophilization or other means, the lyophilized product of Compound A or a physiologically-acceptable salt thereof can comprise a surfactant, a dispersant and the like, and further a part of the solvent for milling.

In the above case, a dispersion medium can be used as a solvent for milling and the milled suspension can be also provided as the present formulation by optionally diluting it without lyophilization.

The formulation of the present invention also includes a formulation which is used up in one shot or in a week or other periods, and a formulation of preparing a suspension in use whose use is limited to a week, a month, or other periods after preparing a suspension.

The dispersion medium used herein means a biocompatible solvent which can make Compound A or a physiologically-acceptable salt thereof dispersed in the liquid formulation, and may include one-ingredient solvent and plural-ingredients solvent as long as the solubility of Compound A in the dispersion medium is preferably 0.4 mg/mL or lower, more preferably 0.1 mg/mL or lower. Specifically, the dispersion medium includes an aqueous solvent as well as an oily solvent such as castor oil, polyoxyethylene castor oil, polyoxyethylene hydrogenated castor oil, and liquid paraffin. And, it may include a mixture of the two or more solvents.

Preferred dispersion medium used herein is an aqueous dispersion medium. The aqueous dispersion medium means an aqueous solvent which comprises 90 w/w % or more water, preferably 95 w/w % or more water, and more preferably 99 w/w % or more water, per the whole of the dispersion medium solvent. Particularly preferred solvent as the dispersion medium is water.

The solvent in the aqueous dispersion medium besides water includes ethanol, glycerin, propylene glycol, fennel oil, phenylethyl alcohol, monoethanolamine, acetic acid, glacial acetic acid, hydrochloric acid, benzyl alcohol, and polyethylene glycol. As mentioned above, however, the dispersion medium used herein does not include a dispersion medium for an oil-in-water emulsion formulation wherein an oil and fat liquid drop encompassing the present drug is dispersed in water.

The dispersion medium used herein may contain an additive such as a dispersant, a surfactant, a wetting agent, a tonicity agent, a buffer agent, a preservative, and a pH adjuster. Preferably, the dispersion medium includes a surfactant and/or a dispersant.

Preferred dispersion medium used herein includes water, and more preferred dispersion medium is water containing either a surfactant or a dispersant, even more preferably water containing both of a surfactant and a dispersant.

In addition, preferred dispersion medium used herein also includes an aqueous solvent containing either a surfactant or a dispersant, and an aqueous solvent containing both of a surfactant and a dispersant.

The pH of the dispersion medium used herein is generally 3-9, preferably 3-8, more preferably 4-7, and particularly preferably 4-6. The pH of the dispersion medium can be adjusted with a pH adjuster mentioned below.

The solvent for milling used herein means a solvent used in wet-milling Compound A or a physiologically-acceptable salt thereof, wherein the solubility of Compound A is preferably 0.4 mg/mL or lower. Specifically, the solvent for milling used herein includes water, a polyalcohol (such as glycerin, propylene glycol and polyethylene glycol), heptane, and hexane. And, it may include a mixture of the two or more solvents. The preferred mixed solvent is an aqueous solvent comprising 90 w/w % or more water per the whole of the solvent and optionally-including the above-defined polyalcohol, and more preferably including 95 w/w % or more water and particularly preferably 99 w/w % or more water per the whole of the solvent. Preferred solvent for milling used herein is water which may contain an additive such as a surfactant, a dispersant, and a salt as appropriate to assist in the milling of Compound A or a physiologically-acceptable salt thereof. The above-mentioned dispersion medium can be used as a solvent for milling.

The formulation of the present invention may be provided after sterilization, wherein the sterilization can be done by, for example, filtrating, radiating, or autoclave-treating a suspension of Compound A or a physiologically-acceptable salt thereof in a dispersion medium. As appropriate, Compound A or a physiologically-acceptable salt thereof, the lyophilized suspension, the dispersion medium, and optionally-added additives may be separately sterilized. And, the whole processes to prepare the present ophthalmic formulation or a part of the processes may be also done in a sterile environment.

Particle sizes in the present invention were measured, for example, in manners explained below, considering the state of particle, the size of particle, etc., but should not be limited thereto.

As for a solid Compound A or a physiologically-acceptable salt thereof dispersed in a suspension formulation, whose particle size is in 1 nm-5 μm, preferably 10 nm-5 μm; the measurement of the particle size thereof was done by diluting the suspension formulation with a dispersion medium to adjust the content of Compound A or a physiologically-acceptable salt thereof in the suspension formulation to about 200-500 μg/mL, and then measuring the diluted sample with a measuring instrument, Zeta Sizer nano S (Malvern Instruments Ltd, Malvern UK). The measurement/calculation of particle size was done by dynamic light scattering, with Material RI and Dispersant RI of 1.33, and the average of the calculated Z-average value of particle size was shown as the measured particle size.

As for a solid Compound A or a physiologically-acceptable salt thereof dispersed in a suspension formulation, whose particle size is 5 μm or more; the measurement of the particle size thereof was done by diluting the suspension formulation with a dispersion medium to adjust the content of Compound A in the suspension formulation to about 10-50 μg/mL, dispersing the diluted suspension with a ultrasonic (15 seconds) and a stirrer (speed: 1200 rpm), measuring the dispersed sample with a laser diffraction particle size analyzer: HEROS/BR-multi and a wet dispersion unit: CUVETTE (Sympatec GmbH) [range R3, using 50 mL cell, trigger condition (time base: 1000.00 ms, assay: 10 s actual time)], and calculating the x50 value of particle size by calculation mode HRLD. The x50 value was shown as the measured value.

As for a dry-milled Compound A or a physiologically-acceptable salt thereof, the measurement of the particle size thereof was done with a laser diffraction particle size analyzer: HEROS/BR-multi and a dry dispersion unit (Sympatec GmbH) [range R3, trigger condition (start: ch. 25≥0.5%, stop: ch. 25≤0.5% for 2 seconds or 10 seconds as actual time), dispersive pressure 2.0 bar], and the x50 value calculated by calculation mode HRLD was shown as the measured value.

The surfactant used herein is a material which has a hydrophilic group and a hydrophobic group (lipophilic group) in its molecular; can form a micell, vesicle, or lamellar structure when its concentration is higher than a certain one; can make a polar substance and a non-polar substance mixed uniformly; has an action to reduce surface tension; and has a molecular weight of 6,000 or less; and it is an additive to contribute to moistening of a nano particle of Compound A or a physiologically-acceptable salt thereof. Specific surfactant used herein includes polysorbate 80, polyoxyethylene hydrogenated castor oil, polyoxyethylene castor oil, alkyl diamino ethyl glycine hydrochloride, polyoxyl 40 stearate, glycerin, propylene glycol, sodium chondroitin sulfate, aluminum monostearate, alkylallyl polyether alcohol, cholesterol, sucrose fatty acid ester, sorbitan fatty acid ester, sorbitan sesquioleate, squalane, stearyl alcohol, cetanol, cetomacrogol 1000, diethyl sebacate, sodium dodecylbenzenesulfonate, sorbitan trioleate, nonylphenoxy polyoxyethylene ethanesulfate ester ammonium, polyoxyethylene oleyl amine, polyoxyethylene stearyl ether, polyoxyethylene cetyl ether, polyoxyethylene sorbitan monolaurate, polyoxyethylene sorbeth beeswax, polyoxyethylene nonylphenyl ether, polyoxyethylene polyoxypropylene glycol, polyoxyethylene polyoxypropylene cetyl ether, polyoxyl 35 castor oil, polysorbate 20, polysorbate 60, macrogol 400, macrogol 4000, macrogol 6000, sorbitan monoleate, glyceryl monostearate, sorbitan monostearate, lauryl dimethylamine oxide solution, sodium lauryl sulfate, lauric acid diethanolamide, sodium lauroyl sarcosinate, lauromacrogol, sodium polyoxyethylene laurylether phosphate, and polyoxyethylene oleylether phosphate.

Preferably, it includes polysorbate 80, polyoxyethylene hydrogenated castor oil, polyoxyethylene castor oil, alkyl diamino ethyl glycine hydrochloride, polyoxyl 40 stearate, glycerin, propylene glycol, sodium chondroitin sulfate, aluminum monostearate, macrogol 4000, and macrogol 6000; and more preferably polysorbate 80, alkyl diamino ethyl glycine hydrochloride, and polyoxyethylene hydrogenated castor oil. And, two or more surfactants may be used, preferably 2-3 surfactants. The amount of surfactant is preferably 0.001-5% by weight per the total amount of the suspension.

The dispersant used herein is an additive which is a polymer having a molecular weight of 6,000 or more, and can go into the space between nano particles to contribute to preventing aggregation. Specific dispersant used herein includes carboxy vinyl polymer, polyvinylpyrrolidone (povidone), methylcellulose, hydroxypropyl methylcellulose (hypromellose), hydroxyethyl cellulose, hydroxypropyl cellulose, polyvinyl alcohol, carboxymethylcellulose sodium (carmellose sodium), tyloxapol, gum ghatti, gum arabic, powdered acacia, karaya gum, xanthane gum, aminoalkyl methacrylate copolymer RS, propylene glycol alginate, sodium carboxymethyl starch, powdered agar, dioctyl sodium sulfosuccinate, and dextrin.

Preferably, it includes carboxy vinyl polymer, hydroxyethyl cellulose, polyvinylpyrrolidone (povidone), methylcellulose, hydroxypropyl methylcellulose (hypromellose), polyvinyl alcohol, carboxymethylcellulose sodium (carmellose sodium), and tyloxapol; and more preferably carboxy vinyl polymer, hydroxyethyl cellulose, polyvinylpyrrolidone (povidone), methylcellulose, hydroxypropyl methylcellulose (hypromellose), and polyvinyl alcohol. And, two or more dispersants may be used.

The amount of dispersant is preferably 0.001-5% by weight per the total amount of the suspension.

The wetting agent includes ethanol, oleic acid, magnesium silicate, light anhydrous silicic acid, and choline phosphate.

The tonicity agent includes sodium chloride, potassium chloride, sorbitol, glucose, sucrose, D-mannitol, ethanol, oleic acid, magnesium silicate, light anhydrous silicic acid, and choline phosphate, preferably sodium chloride.

The buffer agent includes sodium phosphate, disodium hydrogen phosphate, sodium dihydrogenphosphate, sodium acetate, citric acid, sodium citrate, sodium bicarbonate, and trometamol, preferably disodium hydrogen phosphate and citric acid.

The preservative includes a quaternary ammonium salt such as benzalkonium chloride, benzethonium chloride, and cetylpyridinium chloride; a p-oxybenzoate such as methyl p-hydroxybenzoate, ethyl p-hydroxybenzoate, propyl p-hydroxybenzoate, and butyl p-hydroxybenzoate; benzyl alcohol; phenethyl alcohol; sorbic acid; and sorbate; chlorhexidine gluconate solution.

The pH adjuster includes hydrochloric acid, citric acid, glacial acetic acid, phosphoric acid, sodium dihydrogenphosphate, sodium hydroxide, potassium hydroxide, sodium carbonate, sodium bicarbonate, and disodium hydrogen phosphate hydrate.

The present ophthalmic suspension formulation optionally-comprising the above-mentioned additives as appropriate can be prepared with Compound A or a physiologically-acceptable salt thereof, in which the amount of Compound A or a physiologically-acceptable salt thereof is generally 1-500 mg, preferably 5-300 mg, more preferably 10-300 mg, more preferably 10-200 mg, particularly preferably 20-300 mg, 25-300 mg, 10-150 mg, or 25-230 mg, per 1 mL of a dispersion medium, but the present invention should not be limited to the above-mentioned amounts.

The pH of the present suspension formulation is generally 3-9, preferably 3-8, more preferably 4-7, and particularly preferably 4-6. The pH of the suspension can be adjusted with the above-mentioned pH adjuster.

The osmotic pressure of the present suspension formulation is generally 20-1000 mOsm, preferably 100-700 mOsm, more preferably 180-500 mOsm, and particularly preferably 200-360 mOsm. The osmotic pressure of the suspension can be adjusted with the above-mentioned tonicity agent.

The above-mentioned osmotic pressure of the suspension can be measured with the supernatant solution that is obtained, for example, by centrifuging the suspension. For example, an osmotic pressure measuring device "OSMOSTAT OM-6040" (ARKRAY, Inc.) can be used for the measurement.

The formulation of the present invention may comprise other active ingredient(s) without inhibiting the pharmacological effect of the present invention.

According to the present invention, it has been found that Compound A or a physiologically-acceptable salt thereof can inhibit the facilitatory action of cell migration by the VEGF stimulation, as shown in the test examples below. Thus, Compound A or a physiologically-acceptable salt thereof in the present formulation is expected to have therapeutic effects for various ophthalmic diseases because the compound has an action inhibiting aldose reductase, an action inhibiting VEGF production, and an action inhibiting the facilitatory action of cell migration by the VEGF stimulation. In addition, the present suspension formulation comprising Compound A or a physiologically-acceptable salt thereof, in particular, has a good transferability to posterior eye segment, and thereby the present suspension formulation is also expected to apply therapeutically to a disease in posterior eye segment for which a drug needs to be administered to posterior eye segment, such as age-related macular degeneration, diabetic retinopathy, diabetic macular edema, macular edema, myopic choroidal neovascularization, retinal vein occlusion, choroidal neovascularization, uveitis, retinitis pigmentosa, proliferative vitreoretinopathy, and central serous chorioretinopathy, but the target disease in the present invention should not be limited to these diseases.

In particular, the formulation of the present invention is expected to apply therapeutically to a disease related to VEGF, a disease developed by VEGF-involvement, or a disease following a disease developed by VEGF-involvement.

In addition, the present formulation is also expected to have significant therapeutic effects when applying the formulation therapeutically to a disease in anterior eye segment for which a drug needs to be administered to anterior eye segment, such as keratitis, conjunctivitis, neovascular glaucoma, dry eye, and cataract, or a disease for which a drug needs to be transported across blood-aqueous barrier (BAB) or cornea.

The dosage and administration of the present ophthalmic suspension formulation should be suitably defined based on the drug efficacy, administration route, symptom, age, body weight, etc. Preferred dosage and administration in the present invention is, for example, administering a suspension formulation comprising 1-500 mg/mL Compound A or a physiologically-acceptable salt thereof in eyedrops, in the amount of 1-2 drops every time for each eye, totally once to about 6 times a day. In general, the amount of one drop in eyedrops is 20-80 µL, preferably 30-50 µL. The administration period in the present invention should be decided depending on the symptom severity or the like, including, for example, one or more weeks, preferably about 1 week-about 4 weeks, and more preferably about 4 or more weeks.

The present formulation may be also used for ophthalmic diseases in mammals besides human beings, such as monkey, cattle, horse, dog, and cat.

EXAMPLES

The present invention is explained in detail in the following by referring to Examples, Reference examples, Comparative examples, Tests, etc., but should not be limited thereto.

Reference Example 1

Preparation of Compound A

Compound A was prepared according to a method described in T. Negoro et. al. *J. Med. Chem.* 1998, 41, 4118-4129. To the crude product thereof (10 g) were added activated carbon (50% wet, 0.8 g) and 2-propanol (101 g), and the reaction solution was heated to its reflux temperature (about 84° C.) and stood at the same temperature for 30 minutes. The reaction solution was filtrated at the same temperature and washed with 2-propanol (13.8 g). The obtained filtrate was heated to 75° C. or higher, cooled to 60° C., stood at 60° C. for one hour, and then cooled to 0° C. The precipitated solid was collected on a filter and dried in vacuo to give Compound A as a white crystal (9.3 g).
XRD; 2θ=11.5, 15.4, 15.7, 16.3, 16.9, 18.2, 19.3, 20.1, 20.9, 21.6, 22.2, 23.3, 24.0, 24.7, 25.1, 26.4, 27.5, 28.4, 28.8, 29.6, 29.9, 30.9, 31.9, 32.4.
Differential scanning calorimetry (DSC) showed an endothermic peak that the extrapolated melting onset temperature is 186.7° C.

The above measurement of powder X-ray diffraction was carried out with Powder X-ray diffraction system XRD-6100 (Shimadzu Corp.) whose each condition was as follows: X-ray tube: CuKα (wave length: 1.54 angstrom), tube voltage: 30.0 kV, tube current: 20.0 mA, drive axis: θ-2θ, measurement range: 5-40 degree, step width: 0.020 degree, speed: 2.00 (degree/min), and counting time: 0.60 second. And the above measurement of differential scanning calorimetry (DSC) was carried out with Thermo Plus 2 (Rigaku Corporation) under flowing air, between 25° C. to 250° C., wherein the sample weighed in an aluminum vessel was about 10 mg, and the rate of temperature increase was 5° C. per minute.

The above-obtained Compound A was grained with a jet mill, changing the mill condition to obtain three Compound A which had different mean particle sizes. The mean particle sizes of the obtained three Compound A were 1.43 µm, 6.29 µm, and 21.98 µm.

The mean particle size of the obtained Compound A which was grained with a jet mill (dry mill) was measured with the above-mentioned laser diffraction particle size analyzer and shown as ×50 value of particle sizes which was calculated in calculation mode LD.

Reference Example 2

Preparation of Dispersion Medium (pH 5.0)

To water solution (a) of 0.9% (w/v) sodium chloride in 0.02 mol/L aqueous disodium hydrogen phosphate was added water solution (b) of 0.9% (w/v) sodium chloride in 0.01 mol/L aqueous citric acid to adjust the pH of solution (a) to 5.0 (addition ratio (a):(b)=about 1:1) to give a pH 5.0 citrate-phosphate buffer. 20 g of hydroxypropyl methylcellulose was dissolved in 380 g of purified water to prepare 400 g of 5% aqueous hydroxypropyl methylcellulose, to which 1600 g of pH 5.0 citrate-phosphate buffer solution was added to prepare 2000 g of 1% aqueous hydroxypropyl methylcellulose solution. 500 mg of 27-33% aqueous alkyl diamino ethyl glycine hydrochloride solution was dissolved in 400 g of the 1% aqueous hydroxypropyl methylcellulose solution, and further 2.5 g of polysorbate 80 was added therein and then the mixture was dissolved. The weight of the solution was made to 500 g by adding the 1% aqueous hydroxypropyl methylcellulose solution, and the pH of the solution was adjusted to 5.0 with 1 mol/L aqueous hydrochloric acid to obtain a dispersion medium (pH 5.0). The composition of the prepared dispersion medium (pH 5.0) is shown below.

TABLE 1

| Ingredient | Amount |
| --- | --- |
| citric acid | 0.76 mg/g |
| disodium hydrogen phosphate | 1.13 mg/g |
| sodium chloride | 7.2 mg/g |
| hydroxypropyl methylcellulose | 9.9 mg/g |
| 27-33% aqueous alkyl diamino ethyl glycine hydrochloride solution | 1 mg/g |
| polysorbate 80 | 5 mg/g |
| hydrochloric acid | minor |

Example 1

Preparation of Ophthalmic Suspension Formulation 4 g of Compound A (mean particle size: 1.43 µm) which was grained with a jet mill, and 12 mL of the dispersion medium (pH 5.0) prepared in Reference example 2 were put into a screw bottle, and the mixture was stirred with a stirrer for 30 minutes. Then, the whole sample mixture was transferred in a milling pot. The screw bottle was washed with 4 mL of the dispersion medium and the washing solution was also put into the milling pot. To each of the plurally-prepared milling pots was added 50 g of zirconia beads having each diameter size defined below. The milling pot was set in a planetary ball mill (LP-4/2, ITO MANUFACTURING CO., LTD.) and the content therein was milled at 300 rpm for 2 hours. Each milled solution was filtered with a sieve to remove the beads, and then defoamed with a stirrer/defoamer "THINKY MIXER AR-250" (THINKY CORPORATION) for 30 seconds to give suspension formulations A1, A2, A3, and B to D.

Suspension formulation A1, A2, and A3: the diameter size of the used beads was 0.5 mm.
Suspension formulation B: the diameter size of the used beads was 2.0 mm.
Suspension formulation C: the diameter size of the used beads was 3.0 mm.
Suspension formulation D: the diameter size of the used beads was 5.0 mm.

2.2 g of the jet-milled Compound A (mean particle size: 1.43 μm, 6.29 μm, or 21.98 μm) and 10 mL of the dispersion medium (pH 5.0) were added into a screw bottle, and stirred with a sterrer for 10 minutes to give Suspension formulation E, F, or G.

Each mean particle size of Compound A suspended in suspension formulations A1 to A3, and B to G was measured by the above-mentioned method. Each of the obtained mean particle sizes was shown below.
Suspension formulation A1: 209.0 nm
Suspension formulation A2: 195.2 nm
Suspension formulation A3: 227.0 nm
Suspension formulation B: 451.2 nm
Suspension formulation C: 609.9 nm
Suspension formulation D: 801.2 nm
Suspension formulation E: 1944 nm
Suspension formulation F: 9560 nm
Suspension formulation G: 20430 nm Reference Example 3

Quantitation Analysis of Drug in Each Ophthalmic Suspension Formulation

To 100 μL of each suspension formulation A1 to A3 and B to G were added 800 μL of 1% HPMC and 100 μL of acetonitrile, and each mixture was shaken with a vortex. 100 μL of each shaken mixture was put into a 10 mL measuring flask, 1% HPMC/acetonitrile (1:1) was added thereto, and the mixture was completely dissolved. The total volume of the solution was accurately adjusted to 10 mL with 1% HPMC/acetonitrile (1:1) to give each analysis sample thereof. Each content of Compound A (which is the combined content of the dissolving Compound A and the suspending Compound A) in suspension formulations A1 to A3, and B to G was analyzed with a ultra high-performance liquid chromatograph (SHIMADZU) using column YMC-Pack Pro C 18 5 μm 150×4.6 mm. The analytical results are shown below.
Suspension formulation A1: 200.1 mg/mL
Suspension formulation A2: 216.2 mg/mL
Suspension formulation A3: 207.1 mg/mL
Suspension formulation B: 211.0 mg/mL
Suspension formulation C: 195.6 mg/mL
Suspension formulation D: 218.8 mg/mL
Suspension formulation E: 135.4 mg/mL
Suspension formulation F: 201.8 mg/mL
Suspension formulation G: 224.5 mg/mL Reference Example 4

Preparation of Dispersion Medium (pH 3.0)

To water solution (c) of 0.9% (w/v) sodium chloride in 0.02 mol/L aqueous disodium hydrogen phosphate solution was added water solution (d) of 0.9% (w/v) sodium chloride in 0.01 mol/L aqueous citric acid to adjust the pH of solution (c) to 3.0 (addition ratio (c):(d)=about 2:8) to give a pH 3.0 citrate-phosphate buffer solution. The obtained pH 3.0 citrate-phosphate buffer was treated in a manner similar to the case of the above pH 5.0 citrate-phosphate buffer solution to obtain a dispersion medium (pH 3.0). The composition of the prepared dispersion medium (pH 3.0) is shown below.

TABLE 2

| Ingredient | Amount |
| --- | --- |
| citric acid | 1.22 mg/g |
| disodium hydrogen phosphate | 0.45 mg/g |
| sodium chloride | 7.2 mg/g |
| hydroxypropyl methylcellulose | 9.9 mg/g |
| 27-33% aqueous alkyl diamino ethyl glycine hydrochloride solution | 1 mg/g |
| polysorbate 80 | 5 mg/g |
| hydrochloric acid | minor |

Reference Example 5

Preparation of Dispersion Medium (pH 8.0)

To water solution (e) of 0.9% (w/v) sodium chloride in 0.02 mol/L aqueous disodium hydrogen phosphate solution was added water solution (f) of 0.9% (w/v) sodium chloride in 0.02 mol/L aqueous sodium dihydrogenphosphate solution to adjust the pH of solution (e) to 8.0 (addition ratio (e):(f)=about 19:1) to give a pH 8.0 phosphate buffer solution. The obtained pH 8.0 phosphate buffer solution was treated in a manner similar to the case of the above pH 5.0 citrate-phosphate buffer solution (provided that 1 mol/L aqueous sodium hydroxide was used instead of 1 mol/L aqueous hydrochloric acid) to obtain a dispersion medium (pH 8.0). The composition of the prepared dispersion medium (pH 8.0) is shown below.

TABLE 3

| Ingredient | Amount |
| --- | --- |
| sodium dihydrogenphosphate | 0.10 mg/g |
| disodium hydrogen phosphate | 2.15 mg/g |
| sodium chloride | 7.2 mg/g |
| hydroxypropyl methylcellulose | 9.9 mg/g |
| 27-33% aqueous alkyl diamino ethyl glycine hydrochloride solution | 1 mg/g |
| polysorbate 80 | 5 mg/g |
| sodium hydroxide | minor |

Example 2

Preparation of Ophthalmic Suspension Formulation

With beads having a diameter of 1.0 mm and the dispersion medium (pH 3.0 of Reference example 4, pH 5.0 of Reference example 2, or pH 8.0 of Reference example 5), suspension formulation H, I, or J was prepared in a manner similar to Example 1. Each pH of the obtained suspension formulations is shown below.
Suspension formulation H (pH 3): 3.09
Suspension formulation I (pH 5): 5.07
Suspension formulation J (pH 7): 7.10

Each mean particle size of Compound A suspended in suspension formulations H, I, and J was measured by the above-mentioned method. Each of the obtained mean particle sizes was shown below.
Suspension formulation H (pH 3): 352.1 nm
Suspension formulation I (pH 5): 263.2 nm
Suspension formulation J (pH 7): 256.0 nm Each content of Compound A in suspension formulations H, I, and J was analyzed in the above-mentioned manner, and the analytical results are shown below.
Suspension formulation H (pH 3): 217.9 mg/mL
Suspension formulation I (pH 5): 220.0 mg/mL
Suspension formulation J (pH 7): 222.4 mg/mL Comparative Example 1

Preparation of Ophthalmic Solution Formulation Comprising Compound A

To a solution of 0.9% (w/v) sodium chloride in 0.1 mol/L aqueous sodium dihydrogenphosphate solution was added a solution of 0.9% (w/v) sodium chloride in 0.1 mol/L disodium hydrogen phosphate solution to adjust the pH of the solution to 8.0, and the solution was diluted 1.25-fold with purified water (hereinafter, defined as "pH 8.0 solution"). To 1 mL of the obtained solution were added 400 μg of the jet-milled Compound A and 0.08 mL of ethanol, and Compound A was dissolved to give solution formulation Z.

Comparative Example 2

Preparation of Ophthalmic Suspension Formulation Comprising [5-[(1Z,2E)-2-methyl-3-phenylallylidene]-4-oxo-2-thioxothiazolidin-3-yl]acetic acid or (2S,4S)-6-fluoro-2',5'-dioxospiro[chroman-4,4'-imidazolidine]-2-carboxamide 2 g of [5-[(1Z,2E)-2-methyl-3-phenylallylidene]-4-oxo-2-thioxothiazolidin-3-yl]acetic acid (hereinafter, defined as "Compound B"), and 6 mL of the dispersion medium (pH 5.0) prepared in Reference example 2 were put into a screw bottle, and the mixture was stirred with a stirrer for 30 minutes. Then, the whole sample mixture was transferred in a milling pot. The screw bottle was washed with 2 mL of the dispersion medium and the washing solution was also put into the milling pot. To the milling pot was added 50 g of beads having a diameter of 1.0 mm. The milling pot was set in a planetary ball mill (LP-4/2, ITO MANUFACTURING CO., LTD.) and the content therein was milled at 300 rpm for 6 hours. The milled solution was filtered with a sieve to remove the beads, and then defoamed with a stirrer/defoamer "THINKY MIXER AR-250" (THINKY CORPORATION) for 30 seconds to give suspension formulation X1. In addition, 1.84 g of (2S,4S)-6-fluoro-2',5'-dioxospiro[chroman-4,4'-imidazolidine]-2-carboxamide (hereinafter, defined as "Compound C"), and 6 mL of the dispersion medium (pH 5.0) prepared in Reference example 2 were put into a screw bottle, and the mixture was stirred with a stirrer for 30 minutes. The obtained sample was treated in a manner similar to the above Compound B to give suspension formulation Y1.

1.1 g of Compound B, and 5 mL of the dispersion medium (pH 5.0) prepared in Reference example 2 were put into a screw bottle, and the mixture was stirred with a stirrer for 10 minutes to give suspension formulation X2. In a similar manner, suspension formulation Y2 was also prepared from Compound C.

Each mean particle size of Compound B and Compound C suspended in suspension formulations X1, Y1, X2, and Y2 was measured in a manner similar to the measurement of mean particle size of Compound A. Each of the obtained mean particle sizes was shown below.
Suspension formulation X1: 555.7 nm
Suspension formulation Y1: 290.8 nm
Suspension formulation X2: 8970 nm
Suspension formulation Y2: 5430 nm Each content of Compound B and Compound C in suspension formulations X1, Y1, X2, and Y2 was analyzed in the above-mentioned manner, and the analytical results are shown below.
Suspension formulation X1: 215.4 mg/mL
Suspension formulation Y1: 214.1 mg/mL
Suspension formulation X2: 187.7 mg/mL
Suspension formulation Y2: 196.8 mg/mL The results of Examples and Reference examples herein are summarized below.

TABLE 4

| Example/Reference example number | Ophthalmic formulation (suspension/solution) | Compound | pH of added dispersion medium | pH of suspension | Mean particle size | Content |
|---|---|---|---|---|---|---|
| Example 1 | A1 | A | 5 | — | 209.0 nm | 200.1 mg/mL |
|  | A2 | A | 5 | — | 195.2 nm | 216.2 mg/mL |
|  | A3 | A | 5 | — | 227.0 nm | 207.1 mg/mL |
|  | B | A | 5 | — | 451.2 nm | 211.0 mg/mL |
|  | C | A | 5 | — | 609.9 nm | 195.6 mg/mL |
|  | D | A | 5 | — | 801.2 nm | 218.8 mg/mL |
|  | E | A | 5 | — | 1944 nm | 135.4 mg/mL |
|  | F | A | 5 | — | 9560 nm | 201.8 mg/mL |
|  | G | A | 5 | — | 20430 nm | 224.5 mg/mL |
| Example 2 | H | A | 3 | 3.09 | 352.1 nm | 217.9 mg/mL |
|  | I | A | 5 | 5.07 | 263.2 nm | 220.0 mg/mL |
|  | J | A | 8 | 7.10 | 256.0 nm | 222.4 mg/mL |
| Reference example 1 | Z | A | 8 | — | — | 400 μg/mL |
| Reference example 2 | X1 | B | 5 | — | 555.7 nm | 215.4 mg/mL |
|  | X2 | B | 5 | — | 8970 nm | 187.7 mg/mL |

TABLE 4-continued

| Example/ Reference example number | Ophthalmic formulation (suspension/ solution) | Compound | pH of added dispersion medium | pH of suspension | Mean particle size | Content |
|---|---|---|---|---|---|---|
| | Y1 | C | 5 | — | 290.8 nm | 214.1 mg/mL |
| | Y2 | C | 5 | — | 5430 nm | 196.8 mg/mL |

—: no analysis

Test 1: Evaluation of Storage Stability with Ophthalmic Suspension Formulation Comprising Compound a With regard to the ophthalmic suspension formulation, the content change of Compound A stored at 37° C. and the particle size change of Compound A stored at 25° C. were evaluated according to the following procedures.

According to the procedure described in Example 1, an ophthalmic suspension formulation was prepared with a dispersion medium (pH 5.0) and beads having a diameter of 0.5 mm. The content of Compound A in the obtained ophthalmic suspension formulation and the mean particle size of the suspending Compound A were analyzed by the above-mentioned method. The analytical results were 220.95 mg/mL and 170.2 nm, respectively. The prepared ophthalmic suspension formulation was stored at 37° C. in a given time, and then subjected to ultrasonication to be homogenized. To 100 µL of the ophthalmic suspension formulation were added 800 µL of 1% HPMC and 100 µL of acetonitrile, and the mixture was shaken with a vortex. 100 µL of the shaken mixture was put into a 10 mL measuring flask, and 2% HPMC/acetonitrile (1:1) was added thereto to adjust the total volume of the solution accurately to 10 mL. The obtained solution was used as an analysis sample of Compound A. Each sample of each store time was analyzed with a ultra high-performance liquid chromatograph (SHIMADZU) using column YMC-Pack Pro C 18 5 µm 150×4.6 mm. The analytical results are shown in FIG. 1.

Subsequently, according to the procedure described in Example 1, an ophthalmic suspension formulation was prepared with a dispersion medium (pH 5.0). In the milling, beads having a diameter of 0.5 mm was used for 2 hours, and then the beads was changed to beads having a diameter of 0.02 mm and the mixture was milled for 2 hours. The content of Compound A in the obtained ophthalmic suspension formulation and the mean particle size of the suspending Compound A were analyzed by the above-mentioned method. The analytical results were 168.5 mg/mL and 180.5 nm, respectively. The prepared ophthalmic suspension formulation was stored at 25° C., and the mean particle size of the sample stored for each period was analyzed by the above-mentioned method. The analytical results are shown in FIG. 1.

FIG. 1 shows that the content of Compound A in the present ophthalmic suspension formulation did not decrease very much even after the storage for 72 hours. And, the mean particle size thereof also did not changed even after the storage for 14 days. This result indicates that the present ophthalmic formulation is chemically and physically stable and does not need to be stored in cold place, i.e., can be stored at ambient temperature.

Test 2: Evaluation of Transferability to Posterior Eye Segment in Rats (I-1) and (I-2)

To both eyes of rat model of diabetes, ophthalmic suspension formulation A1 wherein Compound A was suspended in a generally-tolerated dose as a suspension formulation (200 mg/mL) or ophthalmic solution formulation Z wherein Compound A was dissolved (400 µg/mL) was administered in eyedrops in the amount of 5 µL for one eye (which is a maximum tolerated dose for eyedrops in rats) totally 5 times at intervals of 5 minutes. 60 minutes after the administration, each concentration of Compound A in cornea, retina and plasma was measured.

Eyedrop has a limitation about tolerated volume of one shot, which is different from other dosage forms. Thus, the delivery amount of the drug to the target tissue which is obtained from eyedrop of a maximum tolerated dose is important. The tolerated volume varies depending on animal species, and the maximum volume in rats is 5 µL for one eye.

The solubility of Compound A in water is very low, thus, in preparing an ophthalmic solution formulation thereof, an additive was added to the solution to make the solubility of Compound A higher than the original solubility to prepare ophthalmic solution formulation Z (400 µg/mL).

In addition, *Diabetic Retinopathy, INTECH, Chapter 15 "Prophylactic Medical Treatment of Diabetic Retinopathy"*, Akihiro Kakehashi et al. disclose an experiment of oral repetitive administration of Compound A to SDT rats, wherein the dose of Compound A making the retinal capillary weakened and the VEGF production in retina inhibited is 1.0 mg/kg. In the present test, the dose of Compound A (1.0 mg/kg) was orally repeatedly administered once a day for 21 days. 60 minutes after the final administration, each concentration of Compound A in cornea, retina and plasma was measured. The results are shown in FIG. 2 and FIG. 3.

Figure 2:
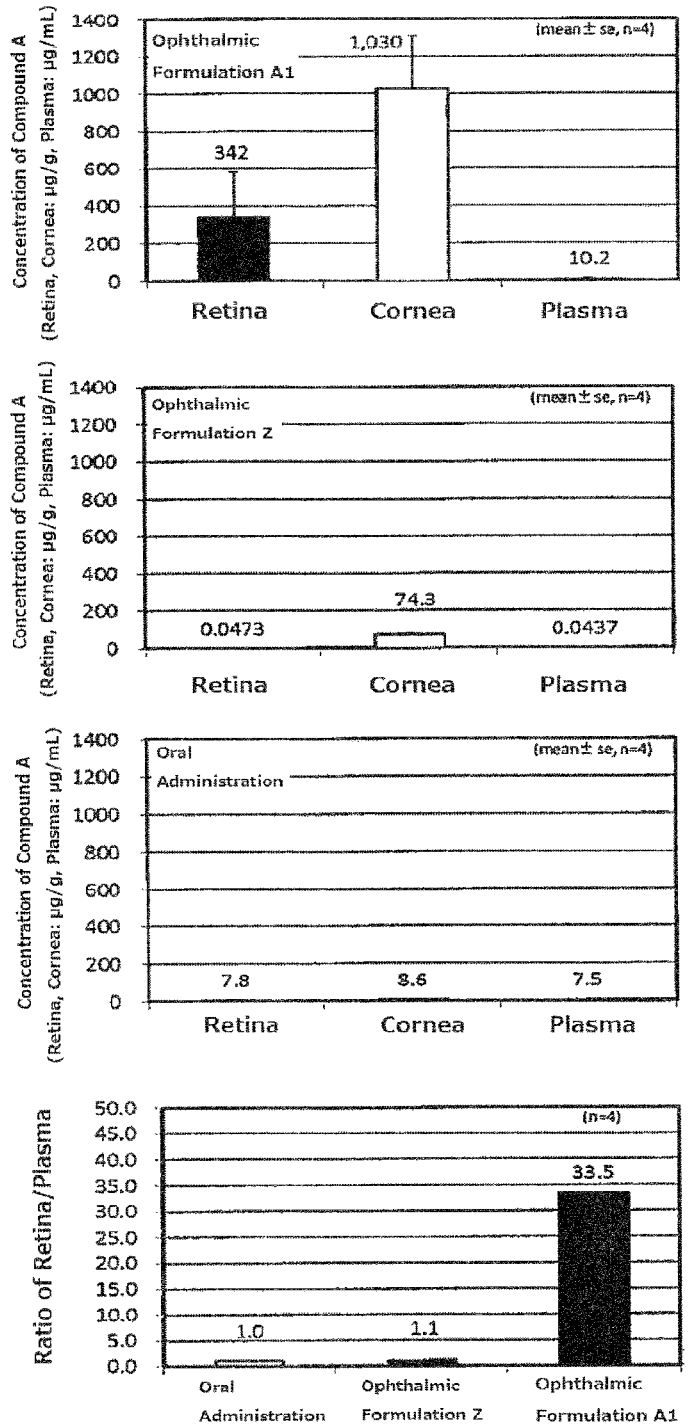
FIG. 2 shows the evaluation of transferability to posterior eye segment in rats (I-1). In the upper three figures among the four figures, the vertical axis denotes the concentration of Compound A in each tissue (the first, second and third graphs show the results of ophthalmic formulation A1, ophthalmic formulation Z, and the oral administration, respectively). The unit of the vertical axis is μg/g for the concentration in retina and cornea, and μg/mL for the concentration in plasma. The abscissa axis denotes each tissue (from left side, retina, cornea, and plasma). In the lowest figure among the four figures, the vertical axis denotes the ratio of retina/plasma, and the abscissa axis denotes each administered formulation (from left side, oral administration, ophthalmic formulation Z, ophthalmic formulation A1). The ratio of retina/plasma denotes "the concentration of Compound A in retina (μg/g))/(the concentration of Compound A in plasma (μg/mL)".
Figure 3:
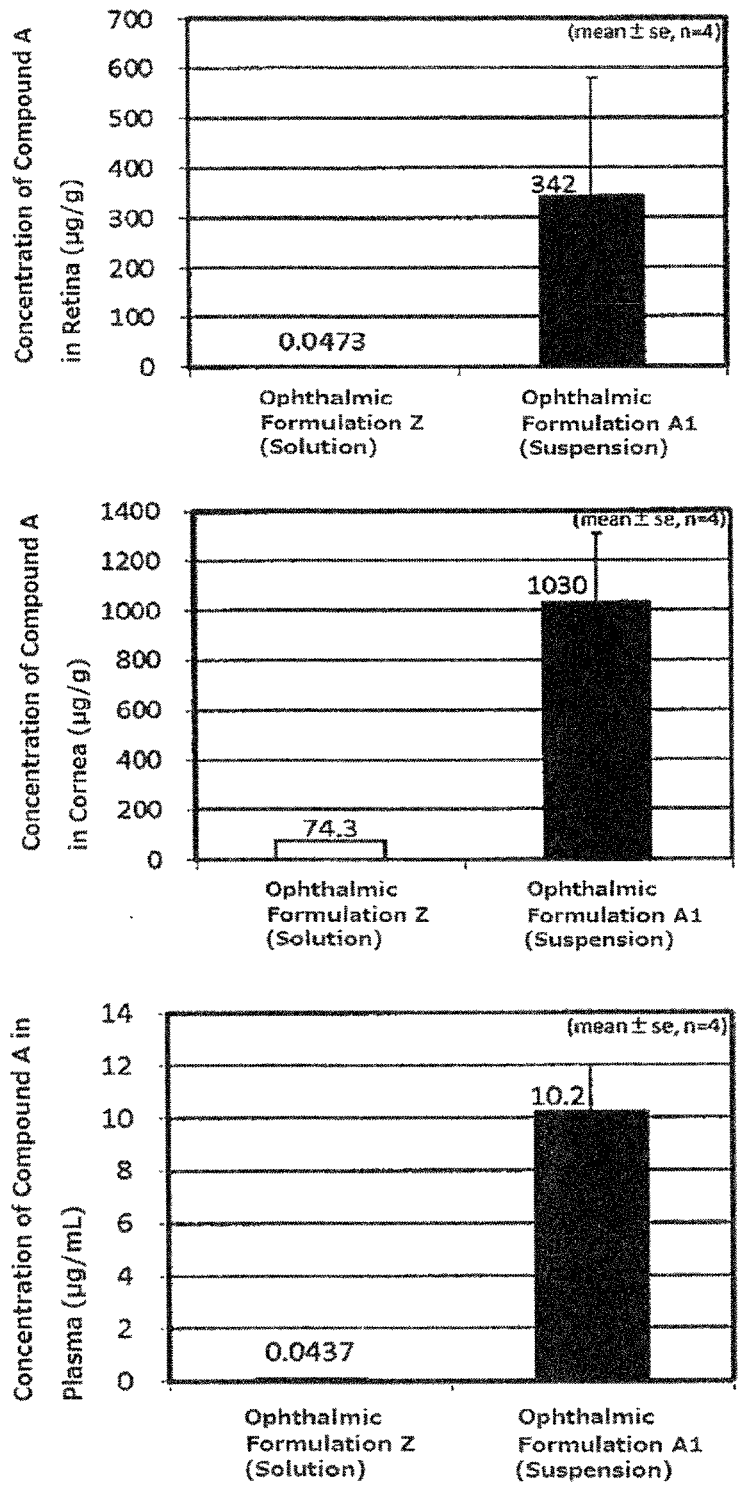
FIG. 3 shows the evaluation of transferability to posterior eye segment in rats (1-2). In each figure, the vertical axis denotes the concentration of Compound A in each tissue (from the upper side, retina, cornea, and plasma). The unit of the vertical axis is μg/g for the concentration in retina and cornea, and μg/mL for the concentration in plasma. The abscissa axis denotes each administered formulation (from left side, ophthalmic formulation Z and ophthalmic formulation A1).

FIG. 2 shows the delivery amount (concentration) of Compound A to plasma, cornea, and retina by the eyedrop administration of ophthalmic suspension formulation A1, the eyedrop administration of ophthalmic solution formulation Z, and the oral repetitive administration. Each delivery ratio of Compound A into plasma, cornea, and retina is shown as follows.

The concentration ratio of Compound A in each tissue by the eyedrop administration of ophthalmic suspension formulation A1 is
plasma:cornea:retina=about 1:101:33.5.

The concentration ratio of Compound A in each tissue by the eyedrop administration of ophthalmic solution formulation Z is
plasma:cornea:retina=about 1:1689:1.

And, the concentration ratio of Compound A in each tissue by the oral repetitive administration is
plasma:cornea:retina=about 1:1:1.

In addition, each retina/plasma ratio in each administration group [retina/plasma ratio=(the concentration of Compound A in retina (µg/g))/(the concentration of Compound A in plasma (µg/mL))] is shown as follows.

The retina/plasma ratio by the administration group of ophthalmic suspension formulation A1=33.5.

The retina/plasma ratio by the administration group of ophthalmic solution formulation Z=1.1.

The retina/plasma ratio by the oral repetitive administration group=1.0.

In the rats to which ophthalmic solution formulation Z was administered in eyedrops, the retina/plasma ratio was 1.1 which was almost the same as the retina/plasma ratio (1.0) by the oral administration. This result suggests that most of ophthalmic solution formulation Z went to blood in general-circulation via nasolacrimal canal and then reached retina.

On the other hand, in the rats to which the present invention, ophthalmic suspension formulation A1 was administered, the retina/plasma ratio was 33.5 which was more than 30-fold higher than the retina/plasma ratio (1.0) that was the result of oral administering an effective dose of Compound A for diabetic retinopathy to SDT rats or the retina/plasma ratio (1.1) that was the result of administering ophthalmic solution formulation Z. This suggested that the ophthalmic suspension formulation can be delivered to retina via a direct delivery route.

Each concentration of Compound A in each tissue in which ophthalmic suspension formulation A1 and ophthalmic solution formulation Z were administered to the rats in Test 2 is shown in FIG. 3. In the rats to which ophthalmic solution formulation Z was administered, the delivery rate to retina was low (0.0473 µg/g) though the concentration of Compound A was higher (400 µg/mL) than the original solubility, i.e., it was not thought that this trial promises the therapeutic effect. On the other hand, in the rats to which ophthalmic suspension formulation A1 was administered, the delivery rate to retina was sufficiently high (342 µg/g) enough to be expected to be the therapeutic effect, in which the concentration of Compound A in the formulation was generally-tolerated dose (200 mg/mL) as a suspension.

The concentration of Compound A in the suspension formulation administered in eyedrops was 500-fold higher [(200 mg/mL)/(400 µg/mL)] than that of the solution formulation, but the amount thereof in retina derived from the suspension formulation was much higher (7230-fold higher [(342 µg/g)/(0.0473 µg/g)]) than that of the solution formulation. On the other hand, as for the delivery to cornea in anterior eye segment and the delivery to plasma, each amount thereof in cornea and plasma derived from the suspension formulation was only 14-fold and 232-fold higher than that of the solution formulation, respectively, though the amount of Compound A in the suspension formulation administered in eyedrops was 500-fold higher than that of the solution formulation.

It has been found that the ophthalmic suspension formulation comprising Compound A can be delivered in more enough concentration of Compound A than by the oral administration via general-circulation or by the eyedrops of the ophthalmic solution formulation. Thus, it is thought that an ophthalmic suspension formulation comprising Compound A or a physiologically-acceptable salt thereof has a sufficient diremption between its effect and its side-effect and hence can make a disease in posterior eye segment including retina treated safely.

Test 3: Evaluation of Transferability to Posterior Eye Segment in Rats (II)

To both eyes of SD rats, ophthalmic formulation A2 was administered in eyedrops in the amount of 5 µL for one eye once, three times, or five times at intervals of 5 minutes. 60 minutes after the administration, each concentration of Compound A in cornea, retina and plasma was measured. The result is shown in FIG. 4

Figure 4:
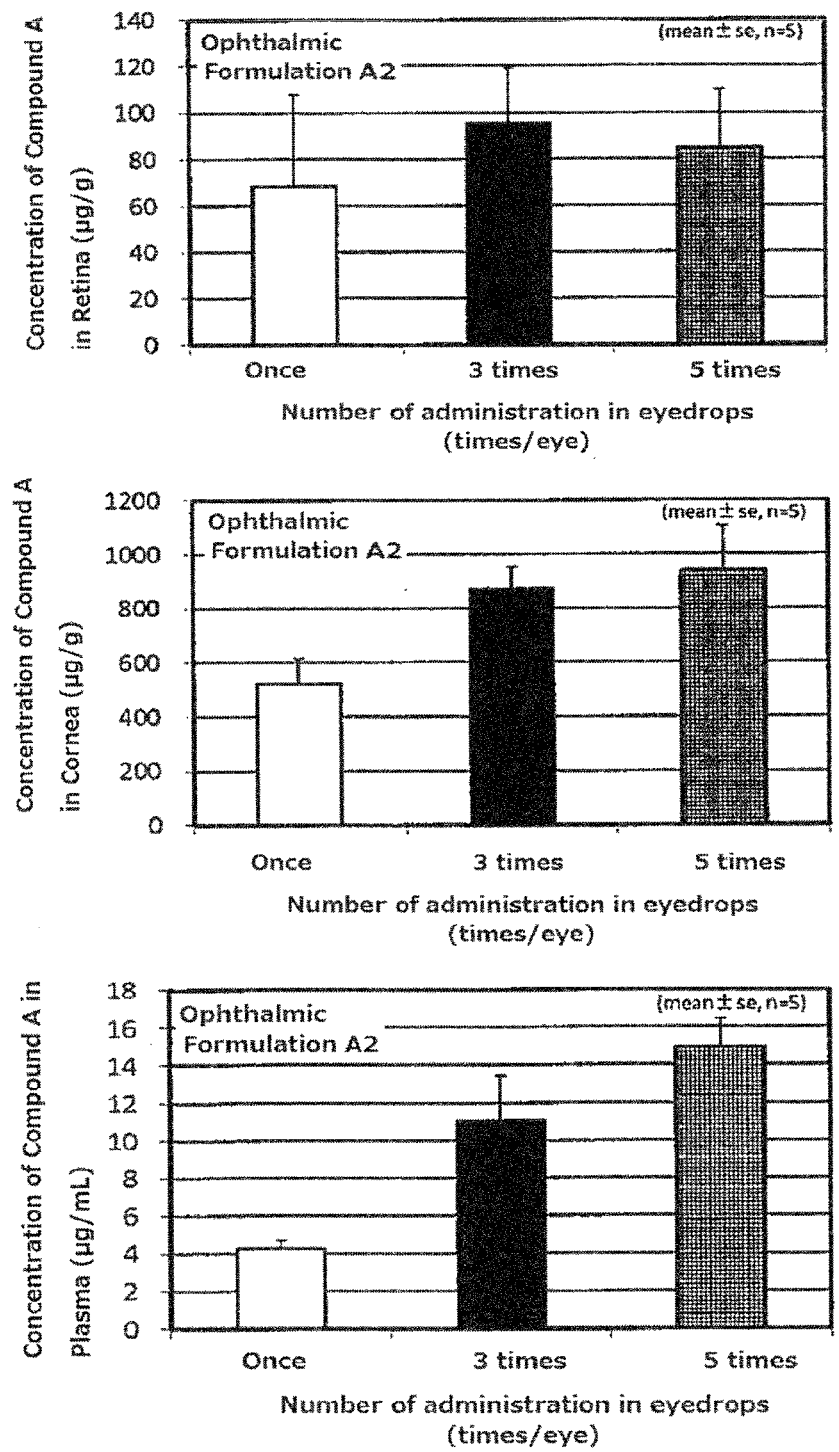
FIG. 4 shows the evaluation of transferability to posterior eye segment in rats (II). In each figure, the vertical axis denotes the concentration of Compound A in each tissue (from the upper side, retina, cornea, and plasma). The abscissa axis denotes the number of administration in eyedrops (from left side, once/eye, 3 times/eye, 5 times/eye).

As shown in FIG. 4, the ophthalmic suspension formulation made the concentration of Compound A in plasma increased with the frequency of the administration. However, the concentration in retina was not influenced by the frequency of the administration, namely a needed amount of Compound A was delivered to retina in one administration. From this result, it has been found that an ophthalmic suspension formulation comprising Compound A or a physiologically-acceptable salt thereof can suppress the elevation in circulating levels and also make the formulation sufficiently delivered into retina, by such few frequency of the administration.

Test 4: Evaluation of Transferability to Posterior Eye Segment in Rats (III)

To both eyes of SD rats, ophthalmic formulation A3 or ophthalmic formulations B-G was administered in eyedrops in the amount of 5 L for one eye once. 60 minutes after the administration, each concentration of Compound A in cornea, retina and plasma was measured. The result is shown in FIG. 5.

In addition, ophthalmic formulation A3 was diluted with the dispersion medium to prepare an ophthalmic suspension formulation having a different concentration of Compound A (20 mg/mL), and then the diluted formulation was administered to SD rats. 60 minutes after the administration, each concentration of Compound A in cornea, retina and plasma was measured (III-2). The result is shown in FIG. 9.

Figure 5:
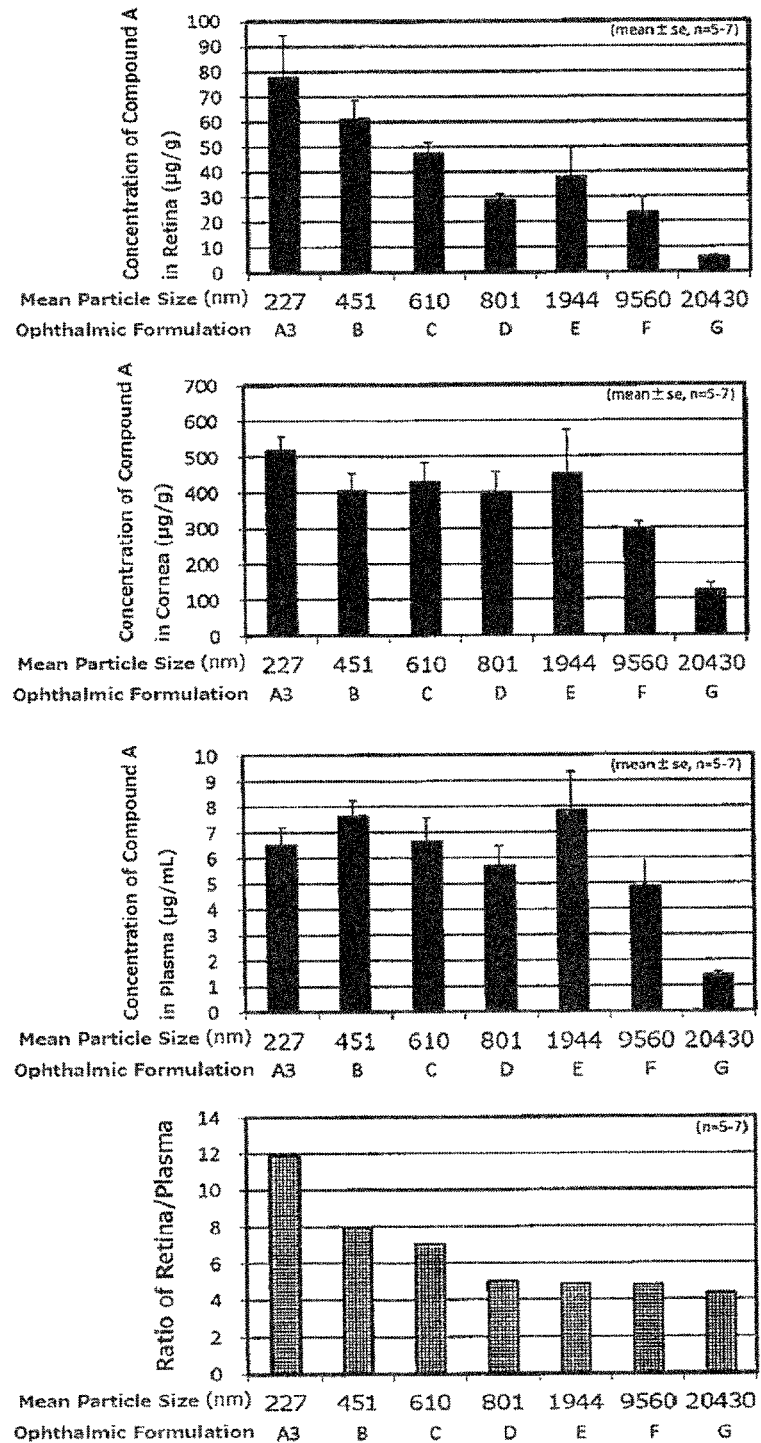
FIG. 5 shows the evaluation of transferability to posterior eye segment in rats (III). In the upper three figures among the four figures, the vertical axis denotes the concentration of Compound A in each tissue (the first, second and third graphs show the results of retina, cornea, and plasma, respectively). The abscissa axis denotes each administered suspension formulation, and each mean particle size (nm) of Compound A in each suspension formulation. In the lowest figure among the four figures, the vertical axis denotes the ratio of retina/plasma, and the abscissa axis denotes each administered suspension formulation, and each mean particle size (nm) of Compound A in each suspension formulation. The ratio of retina/plasma denotes "the concentration of Compound A in retina (μg/g))/(the concentration of Compound A in plasma (μg/mL)".

As shown in FIG. 5, the smaller the mean particle size was, the higher the concentration of Compound A in retina was. In cornea and plasma, however, there was no big difference about the concentration of Compound A as far as the mean particle size is less than 9560 nm. The ophthalmic administration with the suspension formulation showed higher retina/plasma ratio (about 4-12) than that of the oral administration or the ophthalmic administration with the solution (oral administration: 1.0, ophthalmic administration with the solution: 1.1), even for all the ophthalmic suspension formulations having various mean particle sizes. And, the ophthalmic suspension formulation comprising Compound A having a mean particle size of 700 nm or less had a bigger difference between the concentration in retina and the concentration in plasma. Considering this result, it is thought that the ophthalmic suspension formulation can exhibit high effect and also reduce side-effects.

Figure 9:
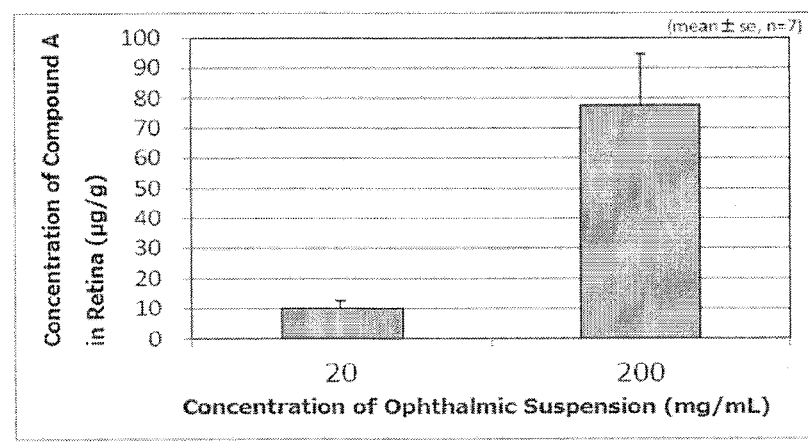
FIG. 9 shows the evaluation of transferability to posterior eye segment in rats (III-2). In each figure, the vertical axis denotes the concentration of Compound A in each tissue (from the upper side, retina, cornea, and plasma). The abscissa axis denotes the concentration of each administered suspension formulation.
Figure 9:
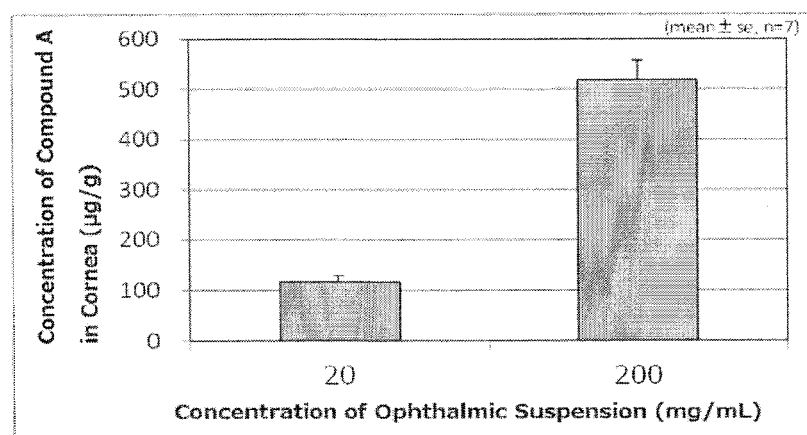
Figure 9:
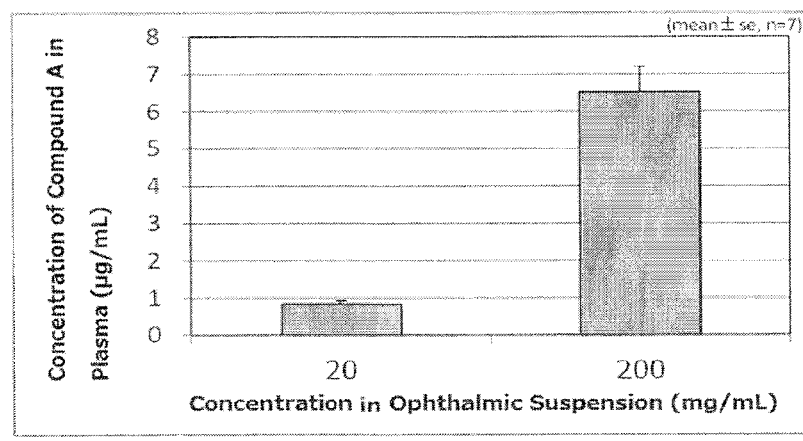

As shown in FIG. 9, the higher the concentration of Compound A in the suspension formulation was, the higher the concentration of Compound A in retina was. It is generally thought that the drug delivery to posterior eye segment depends on the amount of the drug dissolved in water. In this test, however, surprisingly the delivery amount of Compound A to retina increased with the concentration of Compound A in suspended state, regardless of the amount of the dissolved Compound A. And, the ophthalmic administration with the suspension formulation showed higher retina/plasma ratio (about 12) than that of the oral administration or the ophthalmic administration with the solution (oral administration: 1.0, ophthalmic administration with the solution: 1.1), regardless of the suspension concentration.

Test 5: Evaluation of Transferability to Posterior Eye Segment in Rats (IV)

To both eyes of SD rats, ophthalmic formulation H (pH 3), ophthalmic formulation I (pH 5), or ophthalmic formulation J (pH 7) was administered in eyedrops in the amount of 5 µL for one eye once. 60 minutes after the administration, each concentration of Compound A in cornea, retina and plasma was measured. The result is shown in FIG. 6.

Figure 6:
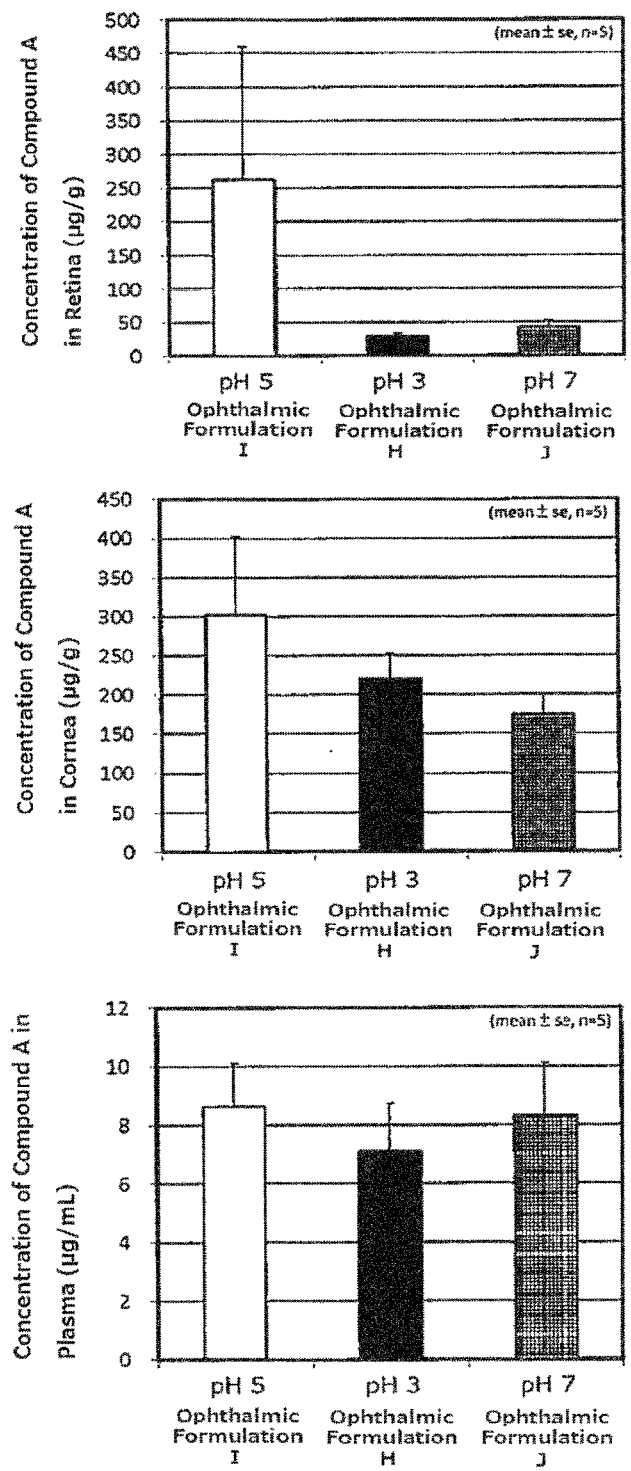
FIG. 6 shows the evaluation of transferability to posterior eye segment in rats (IV). In each figure, the vertical axis denotes the concentration of Compound A in each tissue (from the upper side, retina, cornea, and plasma). The unit of the vertical axis is μg/g for the concentration in retina and cornea, and μg/mL for the concentration in plasma. The abscissa axis denotes each administered suspension formulation, and pH of each suspension formulation.

As shown in FIG. 6, all of ophthalmic formulation I (pH 5), ophthalmic formulation H (pH 3), and ophthalmic formulation J (pH 7) showed a delivery level to retina enough to enable a disease in posterior eye segment to be treated. In particular, ophthalmic formulation I (pH 5) exhibited a very high delivery to retina. However, the delivery to cornea and plasma was not so influenced by pH.

Test 6: Evaluation of Transferability to Posterior Eye Segment in Rats (V)

To both eyes of SD rats, ophthalmic formulation I, ophthalmic formulation F, ophthalmic formulation G, ophthalmic formulation X1, ophthalmic formulation X2, ophthalmic formulation Y1, or ophthalmic formulation Y2 was administered in eyedrops in the amount of 5 µL for one eye once. 60 minutes after the administration, each concentration of Compound A in retina was measured. The result is shown in FIG. 7.

Figure 7:
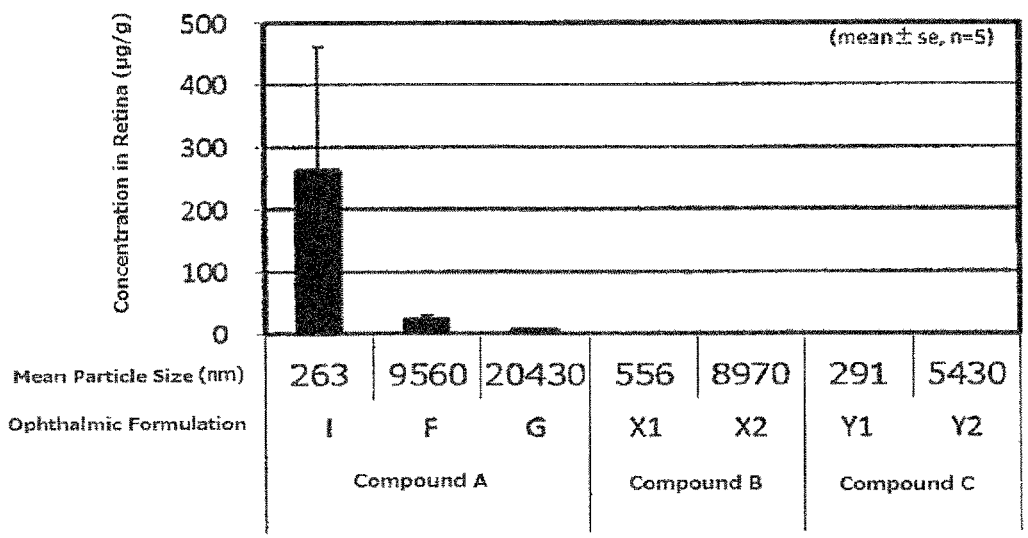
FIG. 7 shows the evaluation of transferability to posterior eye segment in rats (V). In the figure, the vertical axis denotes each concentration of Compound A in retina (μg/g). The abscissa axis denotes each administered suspension formulation, and each mean particle size (nm) of Compound A, B or C in each suspension formulation.

As shown in FIG. 7, the ophthalmic suspension formulation comprising Compound A was delivered to retina much more than the ophthalmic suspension formulation comprising Compound B or C. Even when Compound A in the ophthalmic suspension formulation had a mean particle size of 9560 nm, a needed amount of Compound A was delivered to retina. In case of Compound B or Compound C, however, the compounds having any mean particle size were hardly delivered to retina.

Test 7: Inhibitory Action for Facilitatory Action of Cell Migration by VEGF Stimulation of Compound A The anti-VEGF action of Compound A was evaluated by an experimental method (cell migration assay) described in *J Diabetes Complications.* 2012; 26(5):369-77. In the experiment, a normal human retinal capillary endothelial cell (HREC) which was obtained from Cell System Co., LTD. was used, and a cell culture used herein was CS-C medium (Cell System Co., LTD.). Compound A, Compound B, or Compound C was dissolved in dimethyl sulfoxide (DMSO), each solution was diluted with the cell culture to adjust the concentration in DMSO to 0.1%, and each 0.1% solution was used in the experiment. As for Lucentis, its formulation stock solution was diluted with the cell culture, wherein the dilution ratio was 50 µL of the formulation stock solution per 4 mL of the cell culture, and the diluted solution was used in the experiment. The HREC was seeded in 6-well plate, and it was incubated until the confluency became 80-90%. 20-24 hours before assaying the cell migration by the VEGF stimulation, the cell culture was changed to a cell culture containing 0.1% fetal bovine serum. Then, the culture cell monolayer was wounded with a 200 µL pipette tip at one point per well, and the width of the wounds were measured with a microscope. After the wound, the cell culture was changed to a cell culture containing VEGF, each aldose reductase inhibitor (Compound A, Compound B, Compound C), or Lucentis, depending on each test condition. About 18 hours after changing the cell culture, each width of the wounds was measured with a microscope, and the anti-VEGF action was evaluated by comparing the width with that of the just-wounded one. The results are shown in FIG. 8.

Figure 8:
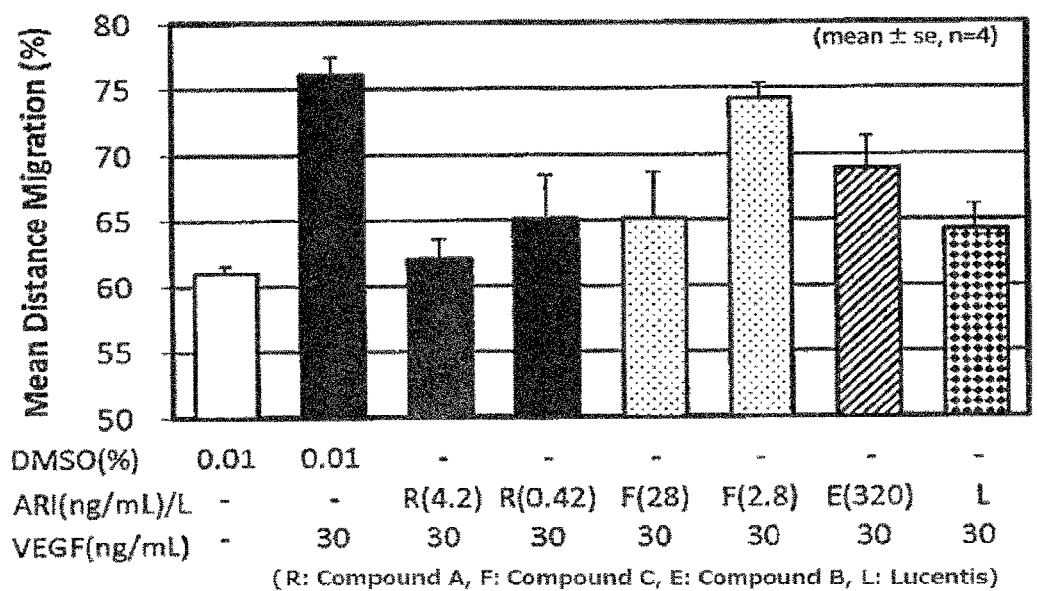
FIG. 8 shows the effect of Compound A about the anti-VEGF action. In the figure, the vertical axis denotes the distance migration of HREC which is a distance migration (%) per the wound width shortly after the wound. The abscissa axis denotes each test condition [DMSO (%), the used drugs (aldose reductase inhibitors or Lucentis® (general name: ranibizumab)) and doses thereof, VEGF concentration (ng/mL)].

As shown in FIG. 8, the results showed that the VEGF stimulation facilitated the HREC migration, and Lucentis and the aldose reductase inhibitors inhibited the migration. The action inhibiting the HREC migration with 1 nM ((0.42 ng/mL)L) Compound A was in the same level as that of 100 nM ((28 ng/mL)/L) Compound C, and more potent than that of 1000 nM ((320 ng/mL)/L) Compound B. In addition, the migration inhibition of Compound A was more potent than those of the other aldose reductase inhibitors, as an action ratio shown in the table shown below. And the migration inhibition of 1 nM Compound A was in the same level as Lucentis which is an anti-VEGF antibody.

TABLE 5

| AR inhibitor | AR inhibitory action, Ki (nM) |
|---|---|
| Compound A | 0.23 (×1.0) |
| Compound C | 1.9 (×8.3) |
| Compound B | 62 (×270) |

*Diabetic Retinopathy, INTECH,* Chapter 15, *"Prophylactic Medical Treatment of Diabetic Retinopathy"*, Akihiro Kakehashi et al. shows that the repetitive oral administration of Compound A to SDT rats which are nonobese type 2 diabetic models can weaken retinal capillary and inhibit producing VEGF in retina, and the finding suggests that the prophylactic administration of Compound A for a disease related to VEGF before facilitating the VEGF production is expected to inhibit the progress to some level. However, the literature did not make it clear that Compound A is effective for the treatment after the onset of the disease, by reducing the action of the already-produced VEGF. In addition, Non-Patent Literature 1 showed only the data of oral administration, but did not show the possibility to inhibit the progress by eyedrop administration.

The present test has made it clear that Compound A or a physiologically-acceptable salt thereof can inhibit the facilitatory action of cell migration by the VEGF stimulation, and also show the anti-VEGF action for already-produced VEGF. This finding suggests that the present invention can treat a disease related to VEGF such as age-related macular degeneration and diabetic retinopathy, after the onset. And, the anti-VEGF action of Compound A is more potent than the other aldose reductase inhibitors, and it is in the same level as Lucentis which is an anti-VEGF antibody formulation.

Reference Example 6

Preparation of Suspension Formulation Samples (1) to (4)

Preparation of Sample (1): According to the steps of Example 1, an ophthalmic suspension formulation comprising Compound A (250 mg/mL) was prepared with the dispersion medium (pH 5.0) and beads having a diameter of 0.5 mm.

Preparation of Sample (2): According to Reference example 2, dispersion medium (pH 5.0) comprising 0.3% polyoxyethylene hydrogenated castor oil was prepared by using polyoxyethylene hydrogenated castor oil instead of polysorbate 80 in the steps of Reference example 2. 15 mL of the dispersion medium and 5 g of Compound A were put into a screw bottle, and the mixture was subjected to ultrasonication for 5 minutes. The whole of content was transferred into a syringe for milling, Star Burst Mini (Sugino Machine Limited), and the screw bottle was washed with 5 mL of the dispersion medium and the washing solution was also put into the syringe. The content in the syringe was milled under a milling pressure of 245 MPa for 30 minutes to prepare an ophthalmic suspension formulation comprising Compound A (250 mg/mL).

Preparation of Sample (3): 1 g of jet-milled Compound A was added to 10 g of glycerin, and the mixture was stirred with a stirrer for 1 hour to prepare a suspension formulation comprising Compound A.

Preparation of Sample (4): 1 g of jet-milled Compound A was added to 10 g of water, and the mixture was stirred with a stirrer for 1 hour to prepare a suspension formulation comprising Compound A.

Test 8: Evaluation of Solubility of Compound A

Each 500 μL of Samples (1) to (4) was centrifuged (150,000 rpm, 10 minutes, 5° C.) with a centrifugal machine, HITACH-GX (Hitachi Koki Co., Ltd.). To 100 μL of the obtained supernatant were added 800 μL of 1% HPMC and 100 μL of acetonitrile or water, and the mixture was shaken with a vortex to give each analysis sample thereof. Each content of Compound A dissolved in each sample was analyzed with a ultra high-performance liquid chromatograph (SHIMADZU) using column YMC-Pack Pro C 18 5 μm 150×4.6 mm. The analytical results are shown in Table 6. Table 6 showed that the percentage of Compound A dissolved in the aqueous suspension was very little.

TABLE 6

|  | Concentration of Compound A dissolved in saturated state (mg/mL) | Percentage (%) of Compound A dissolved in 250 mg/mL suspension | Percentage (%) of Compound A dissolved in 20 mg/mL suspension |
| --- | --- | --- | --- |
| Sample (1) | 0.02 | 0.007 | 0.081 |
| Sample (2) | 0.08 | 0.031 | 0.383 |
| Sample (3) | 0.38 | 0.152 | 1.900 |
| Sample (4) | 0.12 | 0.049 | 0.611 |

Each mean particle size of Compound A suspended in samples (1) and (2) was analyzed in the above-mentioned manner. The results were 244.2 nm and 276.7 nm, respectively. Each particle size in sample (2) which was stored at 25° C. for one month and two months was 277.3 nm and 256.9 nm, respectively.

INDUSTRIAL APPLICABILITY

Considering these examples, reference examples, tests, etc., the ophthalmic formulation of the present invention has a good transferability to posterior eye segment, and can be suitably used for treating ophthalmic diseases such as a disease in posterior eye segment.

The invention claimed is:

1. An ophthalmic formulation, comprising:
an eye drop suspension including Compound A: (R)-(−)-2-(4-bromo-2-fluorobenzyl)-1,2,3,4-tetrahydropyrrolo[1,2-a]pyrazine-4-spiro-3'-pyrrolidine-1,2',3,5'-tetrone or a physiologically-acceptable salt thereof and a dispersion medium in which Compound A or a physiologically-acceptable salt thereof is partially dissolved.

2. The formulation of claim 1, wherein Compound A is present in the formulation.

3. The formulation of claim 1, wherein the mean particle size of Compound A or a physiologically-acceptable salt thereof in the suspension is from 1 nm to 20 μm.

4. The formulation of claim 1, wherein the mean particle size of Compound A or a physiologically-acceptable salt thereof in the suspension is from 10 nm to 20 μm.

5. The formulation of claim 1, wherein the dispersion medium is an aqueous dispersion medium.

6. The formulation of claim 1, wherein the dispersion medium comprises a dispersant and/or a surfactant.

7. The formulation of claim 1, wherein the dispersion medium comprises a dispersant and a surfactant.

8. The formulation of claim 1, wherein the pH of the suspension is 3 to 9.

9. The formulation of claim 1, wherein the osmotic pressure of the suspension is 20 mOsm to 1000 mOsm.

10. The formulation of claim 1, which comprises 1 mg to 500 mg of Compound A or a physiologically-acceptable salt thereof per 1 mL of the suspension.

11. The formulation of claim 1, wherein the ratio of Compound A or a physiologically-acceptable salt thereof dissolved in the suspension to all of Compound A or a physiologically-acceptable salt thereof in the formulation is 0.001% to 10%.

12. The formulation of claim 1, wherein the ratio of Compound A or a physiologically-acceptable salt thereof dissolved in the suspension to all of Compound A or a physiologically-acceptable salt thereof in the formulation is 0.001% to 1%.

13. A method of treating a disease in an anterior eye segment and/or a disease in a posterior eye segment, comprising administering the formulation of claim 1 to an eye of a subject in need thereof.

14. The method of claim 13, wherein the disease is a disease related to VEGF.

15. The method of claim 13, wherein the disease is age-related macular degeneration, diabetic retinopathy, diabetic macular edema, myopic choroidal neovascularization, retinal vein occlusion and/or cataract.

16. A kit, comprising:
(1) a formulation comprising Compound A: (R)-(−)-2-(4-bromo-2-fluorobenzyl)-1,2,3,4-tetrahydropyrrolo[1,2-a]pyrazine-4-spiro-3'-pyrrolidine-1,2',3,5'-tetrone or a physiologically-acceptable salt thereof; and
(2) a formulation comprising a dispersion medium,
wherein mixing formulation (1) and formulation (2) produces the formulation of claim 1.

17. The kit of claim 16, wherein Compound A is present in formulation (1).

18. The kit of claim 16, wherein the mean particle size of Compound A or a physiologically-acceptable salt thereof in formulation (1) is from 10 nm to 20 μm.

19. The kit of claim 16, wherein formulation (1) or formulation (2) further comprises a dispersant and/or a surfactant.

20. A method of treating a disease in an anterior eye segment and/or a disease in a posterior eye segment, comprising:
mixing formulation (1) and formulation (2) of the kit of claim 16 to obtain a mixture; and
administering the mixture to an eye of a subject in need thereof.

21. A method of administering the formulation of claim 1 to an eye of a subject in need thereof, comprising administering the formulation to the anterior of the eye, whereby the Compound A transfers to the posterior of the eye.

22. The method of claim 20, wherein the disease is age-related macular degeneration and/or diabetic retinopathy.

23. The formulation of claim 2, wherein the suspension comprises a dispersant and/or a surfactant.

24. The formulation of claim 23, wherein the suspension comprises a dispersant and a surfactant.

* * * * *